(12) United States Patent
Han

(10) Patent No.: US 8,026,099 B2
(45) Date of Patent: Sep. 27, 2011

(54) LIPID PROFILE AS A BIOMARKER FOR EARLY DETECTION OF NEUROLOGICAL DISORDERS

(75) Inventor: Xianlin Han, Clayton, MO (US)

(73) Assignee: Washington University, St. Louis, MO (US)

(*) Notice: Subject to any disclaimer, the term of this patent is extended or adjusted under 35 U.S.C. 154(b) by 365 days.

(21) Appl. No.: 12/179,809

(22) Filed: Jul. 25, 2008

(65) Prior Publication Data

US 2009/0029473 A1 Jan. 29, 2009

Related U.S. Application Data

(60) Provisional application No. 60/952,083, filed on Jul. 26, 2007.

(51) Int. Cl.
*G01N 33/92* (2006.01)
*G01N 33/487* (2006.01)
(52) U.S. Cl. .................. 436/13; 436/63; 436/71
(58) Field of Classification Search .......... 436/13, 436/63, 71
See application file for complete search history.

(56) References Cited

U.S. PATENT DOCUMENTS

2003/0180959 A1* 9/2003 Han et al. .................. 436/71
2007/0264246 A1* 11/2007 Gross et al. ................ 424/94.1

OTHER PUBLICATIONS

Han et al. Journal of Lipid Research, vol. 47, 2006, pp. 864-879.*
Han et al. Mass Spectrometry Reviews, vol. 24, 2005, pp. 367-412.*
Sun, Shotgun metabolomics approach for the analysis of negatively charged water-soluble cellular metabolites from mouse heart tissue, Anal. Chem., 2007, pp. 6629-6666, vol. 79.
Cheng, Abundance of triacylglycerols in ganglia and their depletion in diabetic mice: Implications for the role of altered triacylglycerols in diabetic neuropathy, J. Neurochem., 2006, pp. 1288-1300, vol. 97.
Han, Shotgun lipidomics of cardiolipin molecular species in lipid extracts of biological samples, J. Lipid res., 2006, pp. 864-879, vol. 47.
Han, Towards fingerprinting cellular lipidomes directly from biological samples by two-dimensional electrospray ionization mass psectrometry, Annal. Biochem., 2004, pp. 317-331, vol. 330.
Jiang, Alkaline methanolysis of lipid extracts extends shotgun lipidomics analyses to the low abundance regime of cellular sphingolipids, Anal. Biochem., 2007, pp. 135-145, vol. 371.
Jiang, Characterization and direct quantitation of sphingoid base-1-phosphates from lipid extracts: A shotgun lipidomics approach, J. Lipid Res., 2006, pp. 1865-1873, vol. 47.
Bligh, A Rapid Method of Total Lipid Extraction and Purification, Canadian Journal of Biochemistry and Physiology, Aug. 1959, 911-917, vol. 37, No. 8, The National Research Council of Canada, Ottawa, Canada.
Puglielli, Alzheimer's Disease: the Cholesterol Connection, Nature Neuroscience, Apr. 2003, 345-351, vol. 6, No. 4, Nature Publishing Group.

* cited by examiner

*Primary Examiner* — Maureen M Wallenhorst
(74) *Attorney, Agent, or Firm* — Polsinelli Shughart PC

(57) ABSTRACT

The present invention relates to compositions and methods for the early detection or monitoring of neurodegenerative diseases and neurological disorders including Alzheimer's disease. The invention provides biomarkers based on lipid profiles of biological samples and methods for using the biomarkers for the detection of neurodegenerative diseases and neurological disorders.

10 Claims, 27 Drawing Sheets

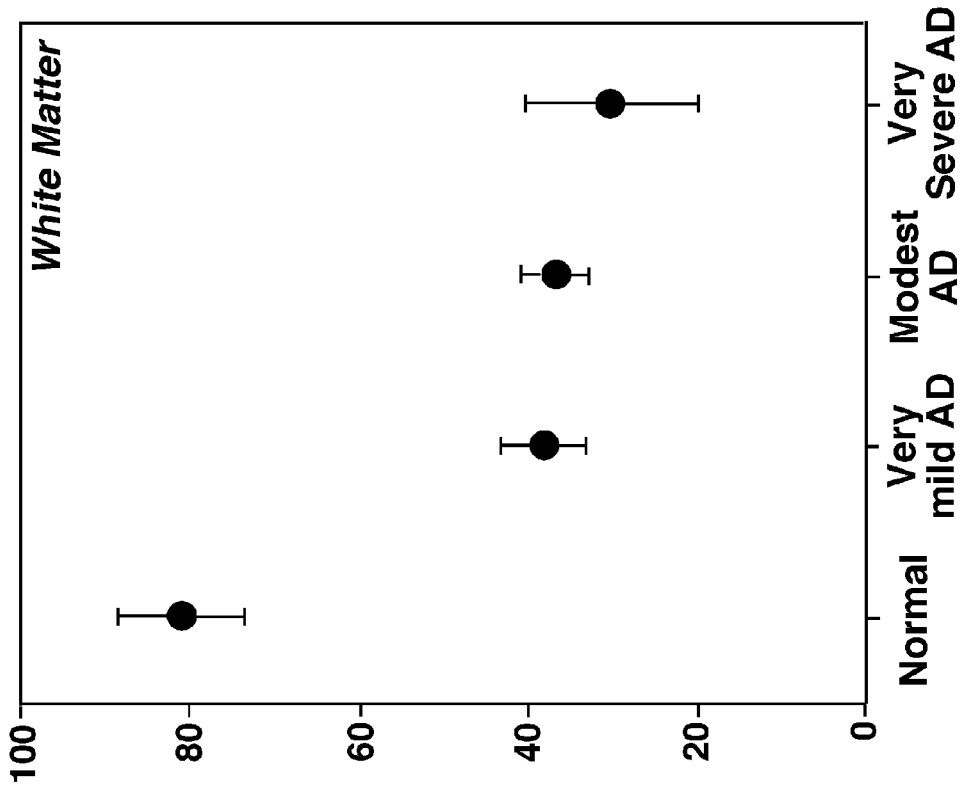
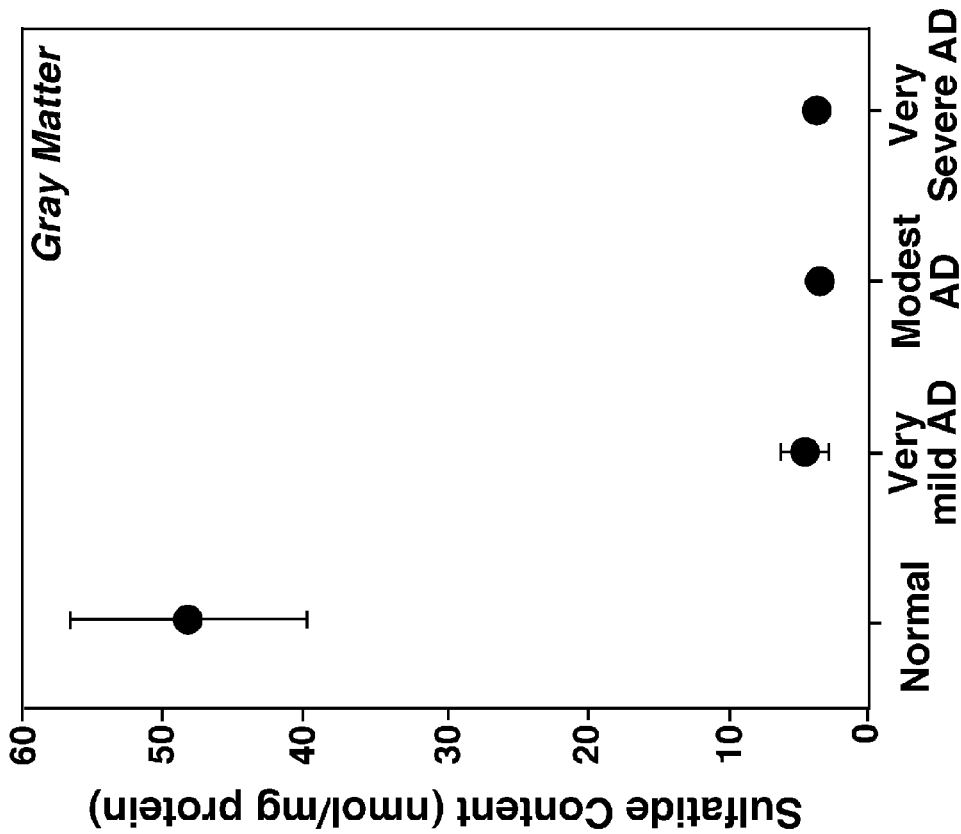
Figure 3A
Figure 3B

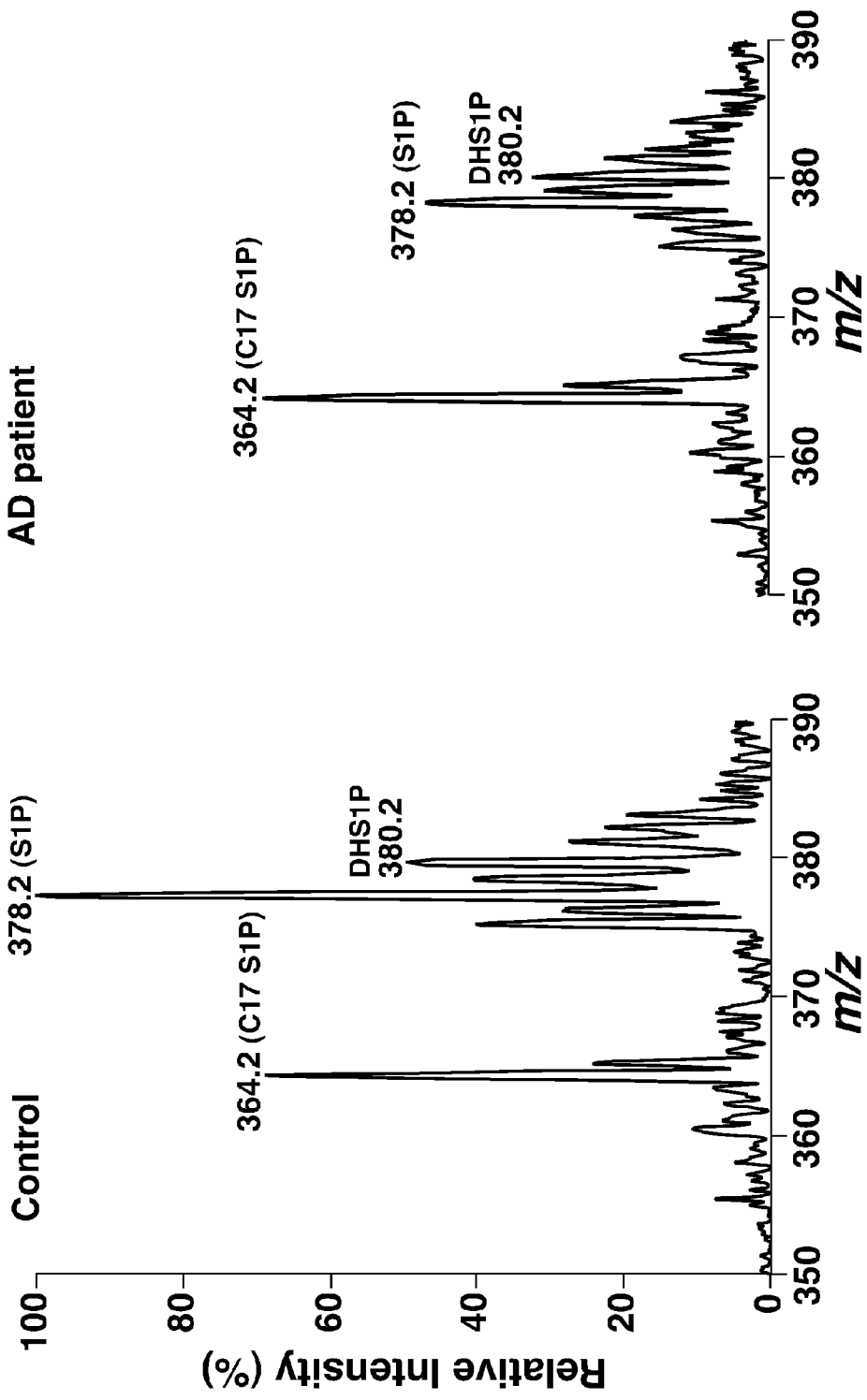

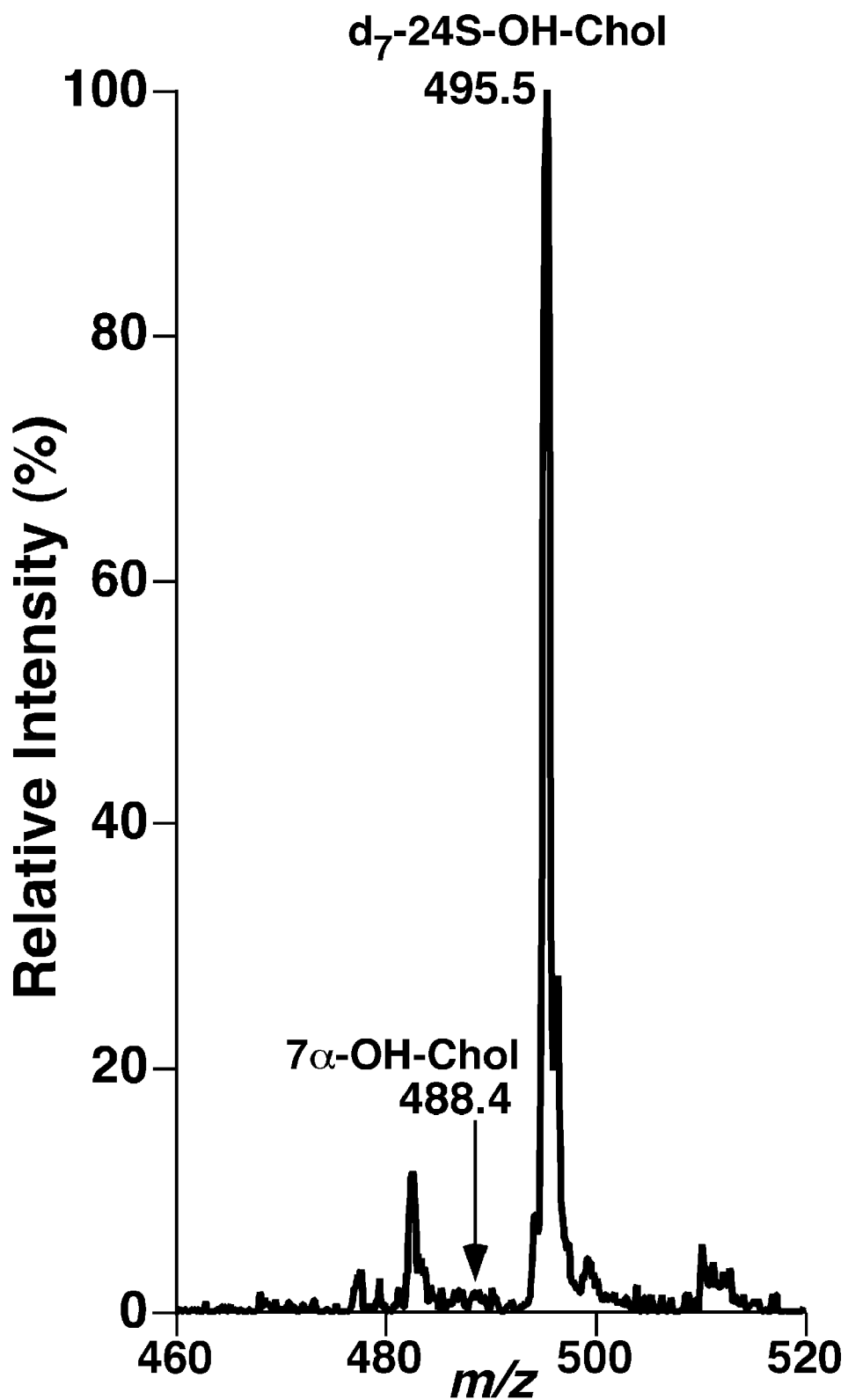

LIPID PROFILE AS A BIOMARKER FOR EARLY DETECTION OF NEUROLOGICAL DISORDERS

CROSS REFERENCE TO RELATED APPLICATIONS

This application claims priority from U.S. Provisional Application Ser. No. 60/952,083 filed on Jul. 26, 2007, which is hereby incorporated by reference in its entirety.

GOVERNMENTAL RIGHTS

This invention was made with government support under 5RO1AG023168 awarded by the National Institute on Aging. The government has certain rights in the invention.

ACKNOWLEDGEMENT OF FEDERAL RESEARCH SUPPORT

The present invention was made, at least in part, with funding from the National Institute on Aging Grant R01AG23168 and National Institute of Health/National Institute on Aging Grant R01AG31675. Accordingly, the United States Government may have certain rights in this invention.

FIELD OF THE INVENTION

The invention relates to biomarkers and methods for the diagnosis and detection of neurological and neurodegenerative diseases, disorders, and associated processes. The invention also relates to methods for determining a lipid profile of a subject.

BACKGROUND OF THE INVENTION

Alzheimer's disease (AD) is the most common dementia among all of the clinically-recognized dementias in the aging population. About 5 million Americans currently suffer from AD, and 22 million other individuals in the world's population are projected to be afflicted by 2025. AD is a neurodegenerative disease of the central nervous system (CNS) that is characterized clinically by progressive loss of memory and other cognitive functions. AD is characterized macroscopically by brain atrophy reflecting neuronal and synaptic loss, and microscopically by the presence of neuritic plaques and neurofibrillary tangles. These insights suggest that treatments to delay the onset, slow the progression, and possibly prevent AD may be possible. A highly sensitive test capable of detecting AD in its earliest stages is needed in order to initiate treatment before significant neurological damage takes place.

To this end, discovery of highly sensitive biomarker(s) for the early diagnosis of AD is extremely important, since even under optimal conditions (i.e., with the presence of informants and thorough evaluation), the sensitivity and specificity of the clinical diagnosis of AD is approximately 80% accurate and currently known biomarkers are of similar reliability. In addition, new biomarkers may be useful in assessing disease progression or response to treatment.

In current clinical practice, the diagnosis of dementia due to AD is based almost entirely on clinical criteria. In addition to genetic analysis, biomarkers have the potential to increase diagnostic accuracy. Although not yet widely used in clinical practice, there are currently several biomarkers for AD that include a decrease in cerebrospinal fluid (CSF) Aβ42, an increase in CSF tau, an increase in isoprostanes, and a decrease in CSF sulfatide, as well as others. The sensitivity and specificity of these markers, at the earliest clinically recognizable stage of AD, has not been shown to be superior to clinically-based assessments at centers specializing in dementia evaluation.

Moreover, an increasingly important therapeutic issue is the identification of patients in the earliest clinically definable stages of AD or even at the pre-clinical stage of AD, so that pharmacotherapy can be maximally effective. Extensive AD pathology (plaques and tangles) develops over a 10 to 20 year period (i.e., pre-clinical AD) prior to any cognitive impairment or major cell loss. The presence of such a pre-clinical AD stage is evidenced by autopsies in which about 30% of subjects who die while cognitively normal in their mid-70's have marked AD pathology (i.e., plaques and tangles), but do not yet have the substantial cell loss that is present in those who die with mild cognitive impairment (e.g., see FIG. 1).

Lipidomics, defined as the large-scale study of the pathways and networks of cellular lipids, is an emerging and rapidly expanding research field, which has been catalyzed by the recognition that cellular lipids play many essential roles in cellular functions, and that the metabolism of individual lipid molecular species or lipid classes is interwoven. One of the major new developments in current lipidomics practice is the multi-dimensional mass spectrometry (MS)-based shotgun lipidomics. Through lipid class-selective intrasource ionization (e.g., see FIG. 2) and subsequent multi-dimensional MS analysis, shotgun lipidomics can fingerprint and quantitate individual molecular species of most of the major and many of the minor lipid classes in cellular lipidomes, which collectively represent >95% of the total lipid mass, and as many as 1,000 lipid molecular species, directly from the solvent extracts of a biological sample. The significance of this technology is that it allows virtually all molecular species of lipids present in biological samples to be screened in an unbiased fashion.

BRIEF SUMMARY OF THE INVENTION

Among the several aspects of the invention is provided a means of diagnosing and monitoring the advent and progress of neurological disorders and neurodegenerative diseases, including Alzheimer's disease. One aspect of the invention provides a biomarker for detecting neurological disorders and neurodegenerative diseases. In an embodiment of the invention, the biomarker is a regression value derived from the relative abundance of each lipid of a lipid profile. In a further embodiment, the biomarker is a lipid profile that comprises at least 1, 2, 3, 4, 5, 6, 7, 8, 9, 10, 11, 12, 13, 14, 15, 16, 17, 18, 19, 20, or more lipid classes. In another embodiment of the invention, the biomarker is a lipid profile that comprises lipids from at least 1, 5, 10, 15, 20, 25, 30, 40, 50, 60, 70, 75, 80, 85, 90, 100, 200, 300, 400, 500, 600, 700, 800, 900, 1000, 1100, or more lipid molecular species.

Another aspect of the invention provides a method for determining a lipid profile of a subject. The lipid profile may be a biological sample from a subject including, but not limited to, blood, plasma, CSF, and brain tissue. In one embodiment of the invention, the lipid profile comprises at least 1, 2, 3, 4, 5, 6, 7, 8, 9, 10, 11, 12, 13, 14, 15, 16, 17, 18, 19, 20, or more lipid classes. In another embodiment of the invention, the lipid profile comprises lipids from at least 1, 5, 10, 15, 20, 25, 30, 40, 50, 60, 70, 75, 80, 85, 90, 100, 200, 300, 400, 500, 600, 700, 800, 900, 1000, 1100, or more lipid molecular species.

DESCRIPTION OF THE DRAWINGS

FIG. 2 depicts the ESI/MS analysis of a lipid extract of human occipital gray matter after intrasource separation. FIG. 2B represents the mass spectrum acquired for anionic lipid species; FIG. 2C represents the mass spectrum acquired for weak anionic species; and FIG. 2D represents the mass spectrum acquired for electrically neutral lipid species. IS denotes internal standard; phosphatidylserine (GPSer); ethanolamine glycerophospholipid (GPEtn); phosphatidylglycerol (GPGro); choline glycerophospholipid (GPCho); galactosylceramide (GalCer); phosphatidylinositol (GPIns); and sulfatide (ST).

FIG. 3 shows the correlation of sulfatide mass content in lipid extracts of temporal gray and white matter with the severity stages of AD dementia. The total content of sulfatide molecular species in chloroform extracts of temporal grey matter (FIG. 3A) and white matter (FIG. 3B) was quantitated using shotgun lipidomics. The data were normalized to the protein content in each tissue sample and are presented as a mean±SEM from six separate subjects per group. The standard error of mean (SEM) is represented by error bars.

FIG. 7 presents the results of shotgun lipidomics analyses for sphingosine-1-phosphate (S1P) in human plasma from controls (FIG. 7A) and AD patients (FIG. 7B). Mass spectra were displayed after being normalized to the internal standard (i.e., C17 S1P).

FIG. 10 shows the results of tandem MS analysis of ethanolamine glycerophospholipids (GPEtn) and lysoGPEtn molecular species in human plasma lipid extracts after treatment with Fmoc-Cl. FIGS. 10A and 10B show the Fmoc-GPEtn molecular species, whereas FIGS. 10C and 10D show the Fmoc-lysoGPEtn molecular species. The spectra in FIGS. 10B and 10D are displayed after being normalized to the internal standards in FIGS. 10A and 10C.

FIG. 11 shows the results of tandem MS analyses of 24S- and 27-OH-Chol after collision induced activation. One hydroxyl or both hydroxyl groups of the oxysterols were derivatized. CID mass spectrometric analyses were performed in the presence of 0.2% acetic acid in the infused solution.

FIG. 12 shows the results of tandem MS analyses of equimolar mixtures of oxysterols by using precursor-ion scanning of m/z 283.3. FIG. 12A shows the precursor ion analysis of an equimolar mixture of 7α-OH-Chol and $d_7$-24S-OH-Chol.

DETAILED DESCRIPTION OF THE INVENTION

Figure 1:
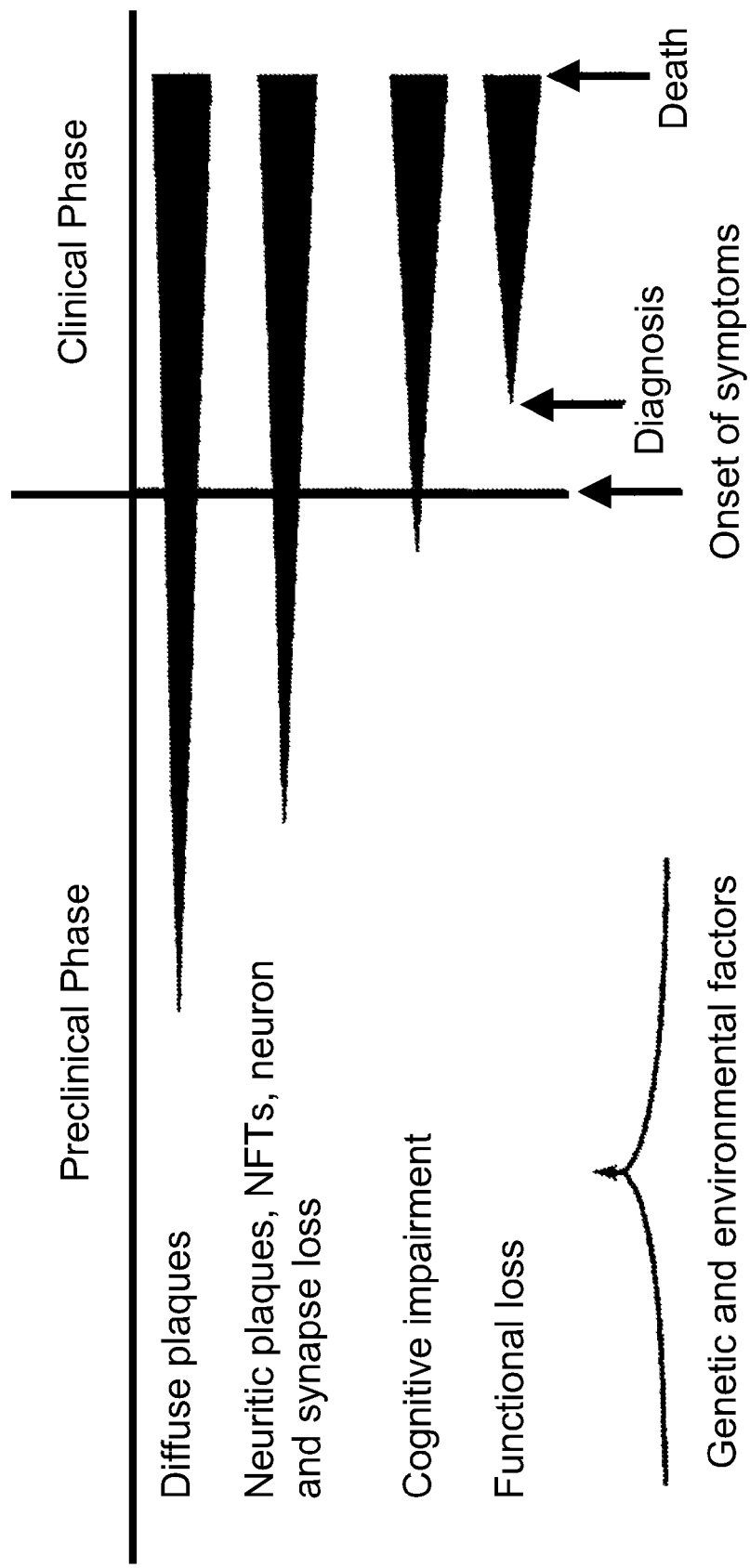
FIG. 1 is a schematic illustration of the different stages of AD pathogenesis. NFT denotes neurofibrillary tangles.
Figure 2A:
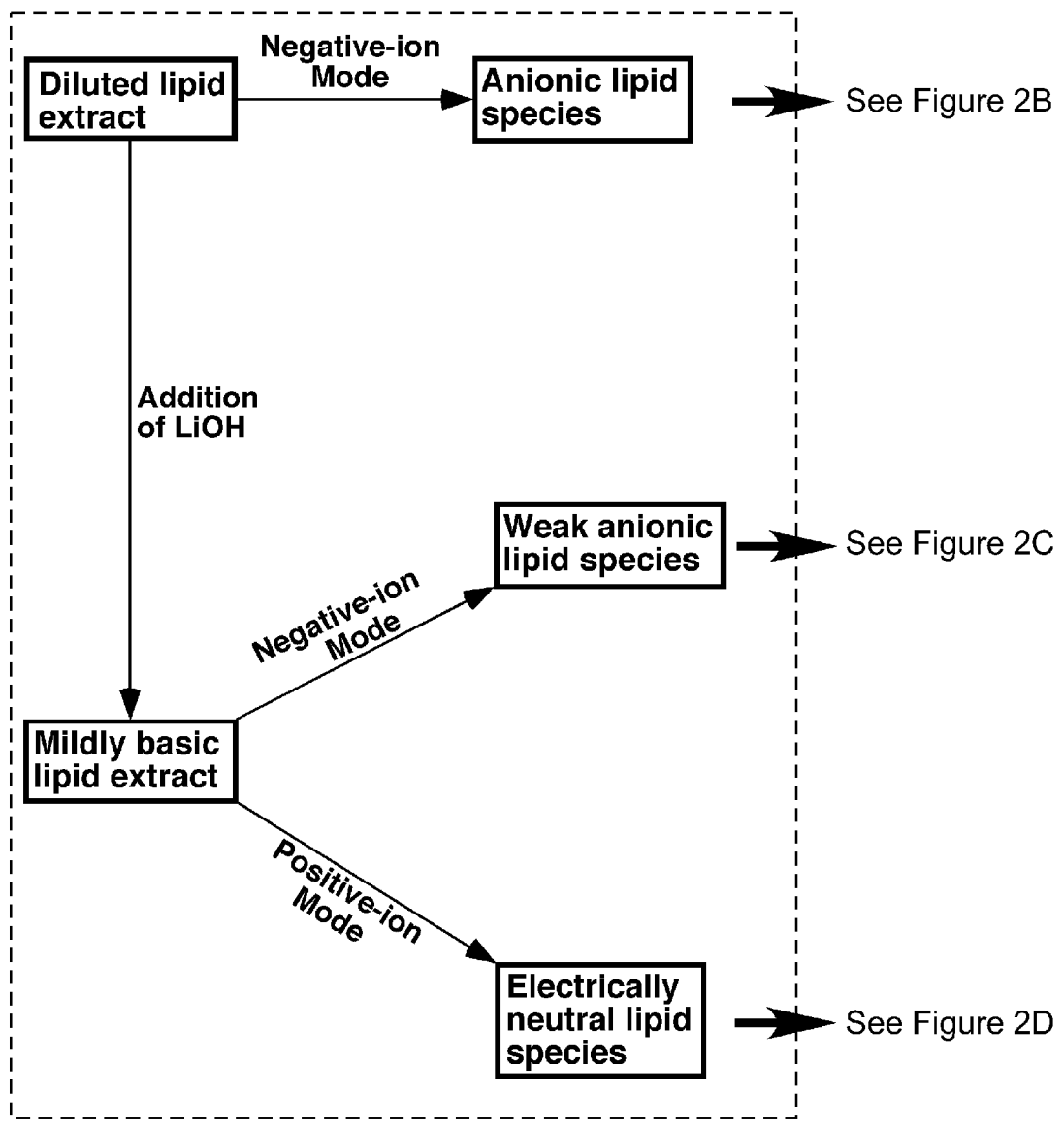
FIG. 2A illustrates a schematic diagram of the procedures used with intrasource separation used to analyze lipids in the positive- or negative-ion mode in the presence or absence of a small amount of LiOH.
Figure 2B:
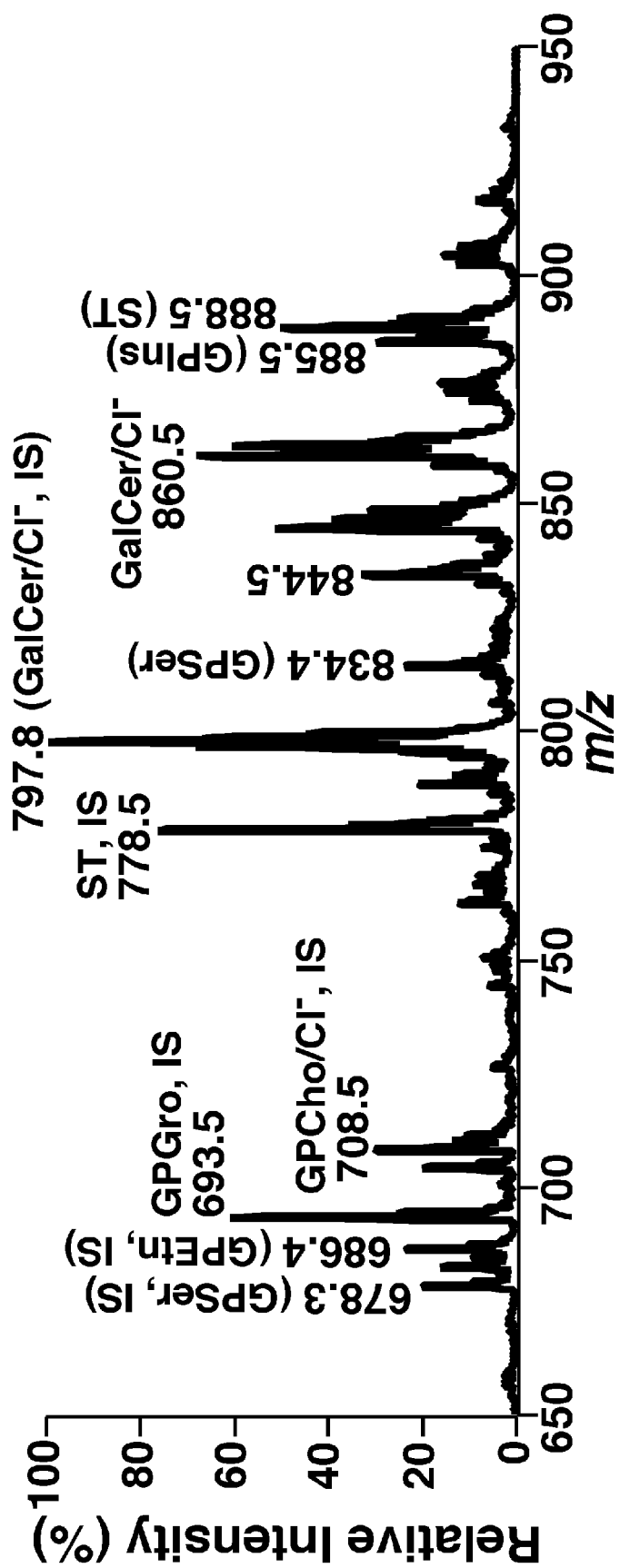
FIGS. 2B through 2D show the corresponding mass spectra acquired under these three conditions, each of which displays a distinct lipid profile of different lipid classes. Key.
Figure 2C:
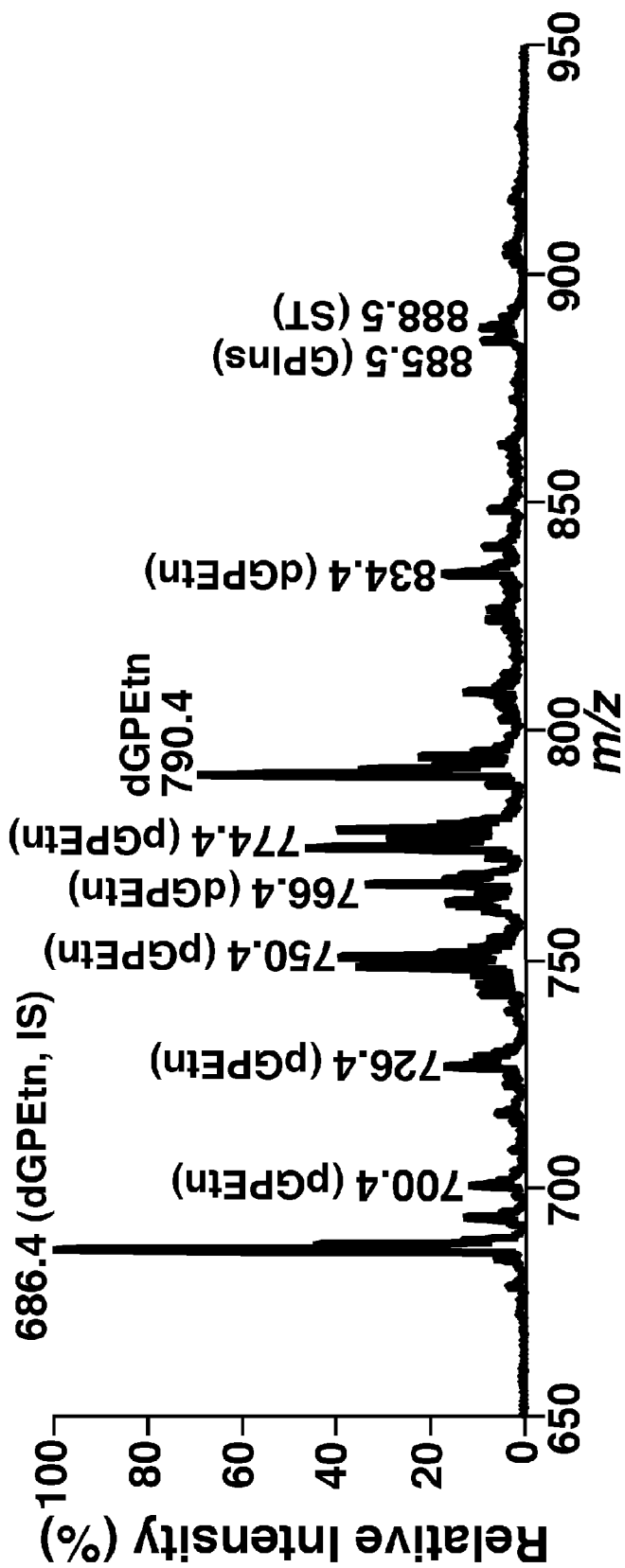
Figure 2D:
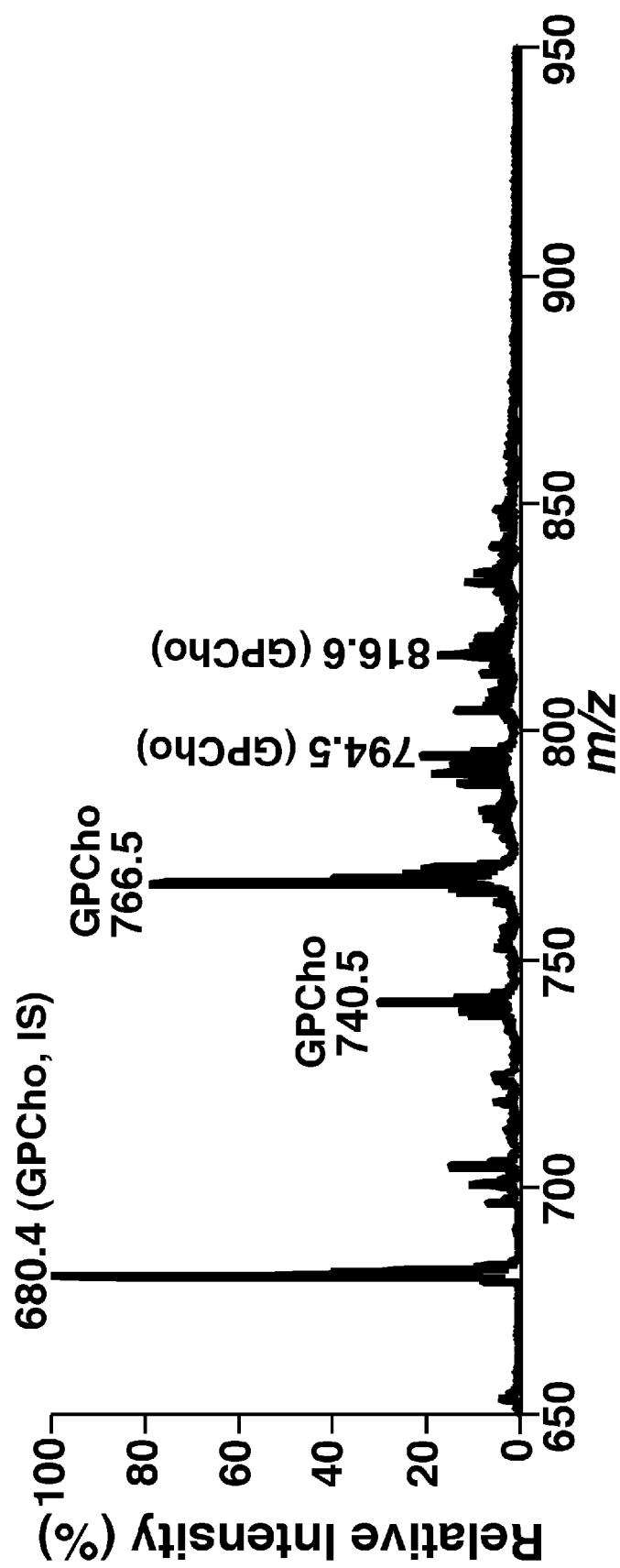

It has been discovered, that the lipid profile of a subject can be used for the early diagnosis of Alzheimer's disease associated dementia as a highly sensitive detection method. An alteration of the entire lipid profile of a subject, including multiple lipid classes and individual molecular species, occurs concurrently with the earliest clinically recognizable stage of Alzheimer's disease (AD) associated dementia, and can be detected from biological samples using shotgun lipidomics technology. In particular, it has been discovered that shotgun lipidomics technology plus shotgun sphingolipidomics can be employed to screen all molecular species of lipids present in biological samples in an unbiased fashion. Specifically, shotgun lipidomics and sphingolipidomics allow the quantitation of over 20 lipid classes and nearly 1,000 individual lipid molecular species from plasma lipid extracts at various stages of AD progression and throughout normal aging. The entire plasma lipid profile provides a much more sensitive detection method in comparison to any single lipid marker for the early diagnosis of AD. The present invention, accordingly, provides methods for the early detection of neurological disorders, monitoring the progression of neurological disorders, and monitoring neurological therapy response using the entire plasma lipid profile of a subject.

I. Compositions of the Invention

The compositions of the invention comprise a biomarker of disorder or disease. The biomarker is a regression value derived from a lipid profile. Generally speaking, a regression value is a single value that is sensitive to changes in abundance of lipid molecular species of a lipid profile, with a regression value of about 1 being indicative of a disorder or a disease state. For example, a regression value of about 0 is indicative of a healthy state, while a regression value of about 0.4, 0.5, 0.6, 0.7, 0.8, 0.9, 1, and more may be indicative of a disorder or disease state. The changed lipid species of the lipid profile includes at least 3 or more lipid molecular species. An embodiment of the invention comprises a lipid profile inclusive of the lipid molecular species of at least one lipid class. Another embodiment comprises a lipid profile including the lipid molecular species of about 2 or more lipid classes. An additional embodiment comprises a lipid profile including about 20 or more lipid classes or about 1,000 or more individual lipid molecular species. Further, an embodiment of the invention comprises a lipid profile that includes the entire lipidome of a biological sample. Methods for determining regression values are illustrated in the Examples.

(a) Lipid Classes

The major groups of lipids are based on chemical properties and chemical structure. Two major groups of lipids include saponifiable and nonsaponifiable lipids. Saponifiable lipids include those having long-chain fatty acids esterified to a backbone molecule such as triacylglycerols, phospholipids, glycolipids, glycerophospholipids, and sphingolipids. Nonsaponifiable lipids include lipids of the cholesterol, carbon-ring compound, and isoprene derivative classes. Additional exemplary lipid classes include choline glycerophospholipid (all subclasses), ethanolamine glycerophospholipid (all subclasses), phosphatidylinositol, phosphatidylglycerol, phosphatidylserine, lyso-glycerophospholipid, lysoethanolamine glycerophospholipid, phosphatidic acid, lyso-phosphatidic acid, sphingomyelin, galactosylceramide, glucosylceramide, gangliosides, sulfatide, free fatty acid, triacylglycerol, diacylglycerol, monoacylglycerols, acyl-CoA, acylcarnitine, cholesterol, cholesterol esters, oxysterols, prostaglandins, ceramide, cardiolipin, and sphingoid base-1-phosphate classes. Each class includes multiple lipid molecular species.

The biomarkers of the invention can be detected in a biological sample using shotgun lipidomics and shotgun sphingolipidomics. Shotgun lipidomics and shotgun sphingolipidomics allow the identification and quantification directly from lipid extracts of more than about 95% of a subject's total lipid mass, representing about a thousand individual molecular species. The majority of lipid classes are identifiable using shotgun lipidomics and shotgun sphingolipidomics. For example, some of the classes of lipids that can be detected by using shotgun lipidomics include choline glycerophospholipid (GPCho), ethanolamine glycerophospholipid (GPEtn), phosphatidylinositol (GPIns), phosphatidylglycerol (GPGro), phosphatidylserine (GPSer), lysoGPCho, lysoGPEtn, phosphatidic acid (GPA), lysoGPA, sphingomyelin (SM), galactosylceramide (GalCer), glucosylceramide, sulfatide, free fatty acid, triacylglycerol (TG), acylcarnitine, cholesterol and cholesterol esters, ceramide, cardiolipin, sphingosine-1-phosphate (S1P), dihydrosphingosine-1-phosphate (DHS1P), sphingosine, and lysoSM, as well as those listed in Tables 1-25. Shotgun lipidomics and sphingolipidomics allow all of the molecular species of lipids present in a biological sample to be screened in an unbiased fashion.

TABLE 1

Exemplary glycerophosphoethanolamine species.
GLYCEROPHOSPHOLIPIDS
Glycerophosphoethanolamine

| | |
|---|---|
| D16:1-16:1 | P18:0-20:4/P18:1-20:3/P16:0-22:4 |
| D14:1-16:1 | P18:1-20:2/P18:0-20:3/P16:0-22:3 |
| P16:0-16:1/P18:0-14:1 | P20:1-18:1/P18:1-20:1 |
| D14:0-18:1/D16:0-16:1 | P18:1-20:0/D18:1-19:1 |
| P16:0-18:2/P18:1-16:1 | D16:2-22:6/P20:0-18:0/P18:0-20:0 |
| P18:1-16:0/P16:0-18:1 | D16:1-22:6 |
| P18:0-16:0/P16:0-18:0 | D16:0-22:6 |
| D16:1-18:2 | D16:0-22:5/D18:1-20:4 |
| D16:0-18:2/D16:1-18:1 | D18:0-20:4/D16:0-22:4 |
| D16:0-18:1 | D18:1-20:2/D16:0-22:3/D18:0-20:3 |

TABLE 1-continued

Exemplary glycerophosphoethanolamine species.
GLYCEROPHOSPHOLIPIDS
Glycerophosphoethanolamine

| | |
|---|---|
| P14:0-22:6 | P18:2-22:6/D18:1-20:1 |
| P16:1-20:4/P14:0-22:5 | P18:1-22:6/D18:0-20:1 |
| P16:0-20:4/P14:0-22:4 | P18:0-22:6/P18:1-22:5/D18:0-20:0 |
| P18:1-18:2/P16:0-20:3 | D18:0-22:5/P18:1-22:4 |
| P18:1-18:1/P18:0-18:2/P16:0-20:2 | P18:0-22:4/P20:0-20:4/P18:1-22:3 |
| P18:0-18:1/P16:0-20:1 | A20:0-20:4/P18:0-22:3 |
| A18:0-18:1 | A18:0-22:3/P18:0-22:2 |
| D14:1-22:6 | D18:2-22:6 |
| D16:2-20:4/D14:1-22:5 | D18:1-22:6 |
| D16:1-20:4 | D18:0-22:6/D18:1-22:5 |
| D16:0-20:4/D18:2-18:2 | D18:1-22:4/D18:0-22:5 |
| D18:1-18:2/D16:0-20:3 | D20:0-20:4/D18:1-22:3/D18:0-22:4 |
| D18:0-18:2/D18:1-18:1/D16:0-20:2 | D20:0-20:3/D18:0-22:3 |
| D18:0-18:1/D16:0-20:1 | D20:0-20:2/D18:0-22:2 |
| P16:0-22:6/D18:0-18:0/P18:2-20:4 | D20:0-20:1/D18:0-22:1 |
| P18:1-20:4/P16:0-22:5 | D20:0-20:0/D18:0-22:0 |

TABLE 2

Exemplary glycerophosphocholine species.
GLYCEROPHOSPHOLIPIDS
Glycerophosphocholine

| | |
|---|---|
| D14:1-14:1 | P18:2-20:1/P20:1-18:2/A18:0-20:4 |
| P14:0-16:0 | A18:0-20:0 |
| D14:0-16:0 | D16:0-22:6/D18:2-20:4 |
| P16:0-16:1/P16:1-16:0/P18:1-14:0 | D18:1-20:4/D16:0-22:5 |
| P16:0-16:0/A16:0-16:1 | D18:2-20:2/D18:0-20:4 |
| A16:0-16:0 | D18:0-20:3 |
| D16:1-16:1/D14:1-18:1 | D18:0-20:2/P18:2-22:6 |
| D16:1-16:0/D14:1-18:0 | D18:0-20:1/P18:1-22:6 |
| D16:0-16:0 | P18:0-22:6 |
| P16:0-18:2/A16:0-18:3 | A18:0-22:6/P18:0-22:5 |
| P16:0-18:1/P18:1-16:0 | D18:2-22:6 |
| P16:0-18:0/P18:0-16:0/A18:1-16:0/A16:0-18:1 | D18:1-22:6/D18:2-22:5 |
| D14:1-20:3/D16:2-18:2/D14:0-20:4 | D18:0-22:6/D20:2-20:4 |
| D16:1-18:2 | D18:0-22:5 |
| D16:0-18:2 | D18:0-22:4/D20:0-20:4/D20:2-20:2 |
| D16:0-18:1 | D18:0-22:3/D20:0-20:3/D18:2-22:1 |
| D16:0-18:0 | D18:0-22:2/D20:0-20:2 |
| P16:0-20:4/P20:4-16:0/P18:2-18:2 | P20:1-22:6 |
| A16:0-20:4 | P20:1-22:4 |
| P18:1-18:1 | P20:0-22:2 |
| P18:0-18:1/P18:1-18:0 | P20:0-22:1 |
| A18:0-18:1/P18:0-18:0 | P21:1-22:6 |
| A16:0-20:0 | P21:1-22:5 |
| D18:2-18:3/D16:1-20:4 | P21:1-22:4 |
| D18:2-18:2/D16:0-20:4 | D20:0-22:5/D20:1-22:4 |
| D18:1-18:2/D16:0-20:3 | D20:0-22:4/D20:2-22:2 |
| D18:0-18:2/D18:1-18:1 | D20:0-22:3/D20:2-22:1 |
| D18:0-18:1 | D20:0-22:2/D20:2-22:0 |
| D18:0-18:0 | D20:0-22:1 |
| P18:1-20:4 | D20:0-22:0 |
| P18:0-20:4 | |

TABLE 3

Exemplary glycerophosphoglycerol species.
GLYCEROPHOSPHOLIPIDS
Glycerophosphoglycerol

| | |
|---|---|
| 16:0-16:1 | 18:2-20:4/16:0-22:6 |
| 16:0-16:0 | 18:1-20:4 |
| 16:1-18:2 | 20:4-20:4/18:2-22:6 |
| 16:0-18:2 | 18:1-22:6 |
| 16:0-18:1 | 18:0-22:6 |
| 18:2-18:3/16:1-20:4 | 20:4-22:6 |
| 18:2-18:2 | 20:3-22:6/20:4-22:5 |
| 18:1-18:2 | 22:6-22:6 |
| 18:1-18:1 | 22:5-22:6 |

TABLE 3-continued

Exemplary glycerophosphoglycerol species.
GLYCEROPHOSPHOLIPIDS
Glycerophosphoglycerol

| | |
|---|---|
| 18:0-18:1 | 22:4-22:6 |
| 16:1-22:6 | |

TABLE 4

Exemplary glycerophosphoserine species.
GLYCEROPHOSPHOLIPIDS
Glycerophosphoserine

| | |
|---|---|
| 14:0-14:0 | P20:0-20:2/P18:0-22:2 |
| 14:0-16:0 | P20:0-20:1/P18:0-22:1 |
| P16:0-16:0 | 18:1-22:6 |
| 16:0-16:1 | 18:0-22:6 |
| 16:0-16:0 | 18:0-22:5 |
| P16:0-18:1 | 20:0-20:4/18:0-22:4 |
| P16:0-18:0 | 20:0-20:3/18:0-22:3 |
| 16:0-18:2 | 20:0-20:2/18:0-22:2 |
| 16:0-18:1 | 20:0-20:1/18:0-22:1 |
| 16:0-18:0 | P20:0-22:5 |
| P18:2-18:2 | P20:0-22:4 |
| P18:1-18:2 | P20:0-22:3 |
| P18:0-18:2 | P20:0-22:2 |
| P18:0-18:1 | 20:3-22:6/P20:0-22:1 |
| P18:0-18:0 | 20:2-22:6 |
| 18:2-18:2 | 20:1-22:6 |
| 18:1-18:2 | 20:0-22:6 |
| 18:0-18:2 | 20:0-22:5 |
| 18:0-18:1 | 20:0-22:4 |
| 18:0-18:0 | 20:0-22:3 |
| P18:0-20:4 | 20:0-22:2 |
| P18:0-20:3 | 20:0-22:1 |
| P18:0-20:2 | 22:6-22:6 |
| P18:0-20:1 | 22:6-22:5 |
| P18:0-20:0 | 22:6-22:4 |
| 18:2-20:4 | 22:6-22:3 |
| 18:1-20:4 | 22:6-22:2 |
| 18:0-20:4 | 22:6-22:1 |
| 18:0-20:3 | 22:6-22:0 |
| 18:0-20:2 | 22:5-22:0 |
| 18:0-20:1 | 22:4-22:0 |
| 18:0-20:0 | 22:3-22:0 |

TABLE 4-continued

Exemplary glycerophosphoserine species.
GLYCEROPHOSPHOLIPIDS
Glycerophosphoserine

| | |
|---|---|
| P18:0-22:5 | 22:2-22:0 |
| P20:0-20:4/P18:0-22:4 | 22:1-22:0 |
| P20:0-20:3/P18:0-22:3 | |

TABLE 5

Exemplary glycerophosphoinositol species.
GLYCEROPHOSPHOLIPIDS
Glycerophosphoinositol

| | |
|---|---|
| 16:0-18:2 | 18:1-20:4 |
| 16:0-18:1 | 18:0-20:4 |
| 16:0-20:4 | 18:0-20:3 |
| 18:1-18:2 | 18:0-20:2 |
| 18:0-18:2 | 18:0-22:6 |
| 18:0-18:1 | 18:0-22:5 |
| 18:0-18:0 | 18:0-22:4 |
| 18:2-20:4/16:0-22:6 | |

TABLE 6

Exemplary phosphatidic acid species.
GLYCEROPHOSPHOLIPIDS
Phosphatidic acid

| | |
|---|---|
| 14:0-14:0 | 18:2-20:4/16:0-22:6 |
| 16:0-16:1 | 18:1-20:4 |
| 16:0-16:0 | 20:4-20:4/18:2-22:6 |
| 16:1-18:2 | 18:1-22:6 |
| 16:0-18:2 | 18:0-22:6 |
| 16:0-18:1 | 20:4-22:6 |
| 18:2-18:2 | 20:3-22:6/20:4-22:5 |
| 18:1-18:2 | 22:6-22:6 |
| 18:1-18:1 | 22:5-22:6 |
| 18:0-18:1 | 22:4-22:6 |
| 16:1-22:6 | |

TABLE 7

Exemplary cardiolipin species.
GLYCEROPHOSPHOLIPIDS
Cardiolipin

| | | | |
|---|---|---|---|
| 18:1-18:1-16:1-16:1 | 20:4-18:2-18:1-16:0 | O-20:4-20:4-18:1-16:1 | 22:6-20:3-18:1-18:1 |
| 18:1-18:1-16:0-16:1 | 20:4-18:1-18:1-16:1 | 22:6-18:3-18:2-18:2 | 22:4-20:4-18:1-18:1 |
| 18:2-18:1-16:0-16:0 | 18:2-18:2-18:1-18:1 | 18:2-18:2-18:2-22:6 | 22:6-20:3-18:1-18:0 |
| 18:2-18:0-16:1-16:0 | 20:4-18:1-18:1-16:0 | 20:4-20:4-18:2-18:2 | 22:4-20:4-18:1-18:0 |
| 18:1-18:1-16:0-16:0 | 20:3-18:1-18:1-16:1 | 20:4-20:4-20:4-16:0 | 22:6-20:4-20:4-18:3 |
| 18:2-18:0-16:0-16:0 | 20:3-18:1-18:1-16:1 | 22:6-20:4-18:1-16:1 | 18:2-18:2-22:6-22:6 |
| 18:1-18:0-16:0-16:1 | 18:2-18:1-18:1-18:1 | 22:6-22:6-16:0-16:0 | 22:6-22:6-20:4-16:0 |
| 20:4-18:2-16:1-16:1 | 18:2-18:1-18:1-18:0 | 22:6-18:2-18:2-18:2 | 20:4-20:4-20:4-20:4 |
| 18:2-18:2-18:2-16:1 | 18:1-18:1-18:1-18:1 | 18:2-18:2-18:2-22:5 | 22:6-20:4-20:4-18:2 |
| 20:4-18:1-16:1-16:1 | 18:1-18:1-18:1-18:0 | 18:1-18:2-18:2-22:6 | 18:2-18:1-22:6-22:6 |
| 20:4-18:2-16:1-16:0 | O-20:4-18:2-18:1-16:1 | 20:4-20:4-18:2-18:1 | 22:6-20:4-20:4-18:1 |
| 18:2-18:2-18:1-16:1 | 22:6-20:4-16:1-16:1 | 18:2-18:2-18:1-22:5 | 18:2-18:0-22:6-22:6 |
| 18:2-18:2-18:2-16:0 | 18:2-18:2-16:1-22:6 | 18:2-18:1-18:1-22:6 | 22:6-22:6-18:1-22:6 |
| 20:4-18:1-16:1-16:0 | 20:4-20:4-18:2-16:1 | 20:4-20:4-18:1-18:1 | 22:6-20:4-20:3-18:1 |
| 18:2-18:1-18:1-16:1 | 18:2-18:2-18:2-20:4 | 18:1-18:1-20:3-20:4 | 16:0-20:3-22:5-22:5 |
| 18:2-18:2-18:1-16:0 | 18:2-18:1-16:1-22:6 | 22:6-18:1-18:1-18:1 | 18:2-20:3-20:3-22:5 |
| 18:1-18:1-18:1-16:2 | 18:2-18:2-16:0-22:6 | 22:6-18:1-18:1-18:0 | 18:0-18:1-22:6-22:6 |
| 18:2-18:1-18:0-16:2 | 20:4-20:4-18:1-16:1 | 20:4-20:2-18:1-18:1 | 18:0-20:3-20:4-22:6 |
| 18:2-18:2-18:0-16:1 | 18:2-18:2-18:2-20:3 | 20:4-20:1-18:1-18:1 | 18:2-20:4-22:6-22:6 |
| 18:2-18:1-18:1-16:0 | 20:4-20:4-18:1-16:0 | 20:4-20:1-18:1-18:0 | 18:2-20:3-22:6-22:6 |
| 18:1-18:1-18:1-16:1 | 22:6-18:1-18:1-16:1 | 18:2-18:3-20:4-22:6 | 22:6-22:6-20:4-18:1 |
| 18:1-18:1-18:1-16:0 | 22:6-18:2-18:1-16:0 | 22:6-20:4-20:4-16:1 | 18:2-20:2-22:6-22:6 |
| 18:0-18:1-18:1-16:1 | 18:2-18:2-18:1-20:3 | 22:6-22:6-18:2-16:1 | 22:6-22:6-20:4-18:1 |
| 18:0-18:1-18:1-16:0 | 20:4-18:2-18:1-18:1 | 18:2-18:2-20:4-22:6 | 22:6-20:4-20:4-20:3 |

TABLE 7-continued

Exemplary cardiolipin species.
GLYCEROPHOSPHOLIPIDS
Cardiolipin

| | | | |
|---|---|---|---|
| 18:0-18:0-18:1-16:1 | 22:6-18:1-18:1-16:0 | 18:2-20:4-20:4-20:4 | 20:4-20:4-22:6-22:6 |
| O-18:2-18:1-18:1-16:1 | 18:1-18:2-18:2-20:2 | 22:6-20:4-20:4-16:0 | 18:2-22:6-22:6-22:6 |
| O-18:1-18:1-18:1-16:2 | 20:4-18:1-18:1-18:1 | 22:6-22:6-18:1-16:1 | 20:4-20:4-22:6-22:5 |
| O-18:2-18:1-18:0-16:2 | 18:1-18:2-18:2-20:1 | 18:2-18:2-20:3-22:6 | 18:2-22:6-22:6-22:5 |
| O-18:2-18:2-18:0-16:1 | 18:1-18:1-18:2-20:2 | 22:6-20:4-18:2-18:1 | 22:6-22:6-22:6-18:1 |
| 20:4-20:4-16:1-16:1 | 20:4-18:1-18:1-18:0 | 18:2-18:2-20:3-22:6 | 22:6-22:6-20:4-20:3 |
| 20:4-20:4-16:1-16:0 | 20:3-18:1-18:1-18:1 | 18:1-18:2-20:2-22:6 | 20:4-20:3-22:6-22:5 |
| 20:4-18:2-18:2-16:1 | 18:1-18:1-18:2-20:1 | 22:6-20:4-18:1-18:1 | 22:6-22:6-22:6-22:6 |
| 18:2-18:2-18:2-18:2 | 18:1-18:1-18:0-20:3 | 18:2-18:2-20:2-22:6 | 22:6-22:6-22:6-22:5 |
| 20:4-18:2-18:1-16:1 | 20:4-18:1-18:0-18:0 | 18:1-18:2-20:1-22:6 | 22:6-22:6-22:6-24:7 |
| 18:2-18:2-18:2-18:1 | 20:3-18:1-18:1-18:0 | 22:6-20:4-18:1-18:0 | |

TABLE 8

Exemplary lyso-glycerophosphoethanolamine species.
GLYCEROPHOSPHOLIPIDS
Lyso-glycerophosphoethanolamine

| | |
|---|---|
| 14:0 | P18:1 |
| 15:1 | P18:0 |
| 15:0 | P19:3 |
| 16:2 | P19:2 |
| 16:1 | P19:1 |
| 16:0 | P19:0 |
| 17:2 | P20:5 |
| 17:1 | P20:4 |
| 18:2 | P20:3 |
| 18:1 | P20:2 |
| 18:0 | P20:1 |
| 19:2 | P20:0 |
| 19:1 | P21:4 |
| 19:0 | P21:3 |
| 20:4 | P21:2 |
| 20:3 | P21:1 |
| 20:2 | P21:0 |
| 22:6 | P22:6 |
| 22:5 | P22:5 |
| 22:4 | P22:4 |
| P14:1 | P22:3 |
| P14:0 | P22:2 |
| P15:1 | P22:1 |
| P15:0 | P22:0 |
| P16:1 | P24:5 |
| P16:0 | P24:4 |
| P17:2 | P24:3 |
| P17:1 | P24:2 |
| P17:0 | P24:1 |
| P18:3 | P24:0 |
| P18:2 | |

TABLE 9

Exemplary lyso-glycerophosphocholine species.
GLYCEROPHOSPHOLIPIDS
Lyso-glycerophosphocholine

| | |
|---|---|
| 17:0 | 20:2 |
| 14:1 | 20:1 |
| 14:0 | 20:0 |
| A16:0 | 22:6 |
| 16:1 | 22:5 |
| 16:0 | 22:4 |
| 18:2 | 22:3 |
| 18:1 | 22:2 |
| 18:0 | 22:1 |
| 20:4 | 22:0 |
| 20:3 | |

TABLE 10

Exemplary lyso-cardiolipin species.
GLYCEROPHOSPHOLIPIDS
Lyso-cardiolipin

| | |
|---|---|
| 18:2-18:2-18:2 | 18:2-22:6-22:6 |
| 18:2-18:2-18:1 | 18:1-22:6-22:6 |
| 18:2-18:1-18:1 | 18:1-22:6-22:5 |
| 18:0-22:6-22:6 | 18:2-18:2-20:4 |
| 18:2-16:1-22:5 | 18:1-16:1-22:6 |
| 16:1-20:4, | 18:2-18:3, |
| 16:2-20:3 | 18:2-18:2-20:3 |
| 18:2-18:1-20:4 | 16:0-20:4, |
| 16:1-20:3, | 16:2-20:2, |
| 18:2-18:2, | 18:1-18:3 |
| 18:2-18:2-20:2 | 18:2-18:1-20:3 |
| 16:0-20:3, | 16:1-20:2, |
| 16:2-20:1, | 18:1-18:2, |
| 18:0-18:3 | 18:2-18:2-22:6 |
| 16:0-20:2, | 16:1-20:1, |
| 18:0-18:2, | 18:1-18:1 |
| 18:2-18:1-22:6 | 16:0-20:1, |
| 18:0-18:1 | 18:1-18:1-22:6 |
| 18:2-18:0-22:6 | 18:0-18:0 |

TABLE 11

Exemplary triacylglyceride species.
GLYCEROLIPIDS
Triacylglyceride

| | | | |
|---|---|---|---|
| C51:3/C52:10 | C48:0/C49:7 | C53:2/C54:9 | C58:5/C59:12 |
| C44:3 | C49:6 | C53:1/C54:8 | C58:4/C59:11 |
| C44:2 | C49:5 | C53:0/C54:7 | C58:3/C59:10 |
| C44:1 | C49:4 | C54:6 | C58:2/C59:9 |
| C44:0/C45:7 | C49:3/C50:10 | C54:5/C55:12 | C58:1/C59:8/C60:15 |
| C45:6 | C49:2/C50:9 | C54:4/C55:11 | C58:0/C59:7/C60:14 |
| C45:5 | C49:1/C50:8 | C54:3/C55:10 | C59:6/C60:13 |
| C45:4 | C49:0/C50:7 | C54:2/C55:9 | C59:5/C60:12 |
| C45:3 | C50:6 | C54:1/C55:8 | C59:4/C60:11 |
| C45:2 | C50:5 | C54:0/C55:7 | C59:3/C60:10 |
| C45:1/C46:8 | C50:4 | C55:6 | C59:2/C60:9 |
| C45:0/C46:7 | C50:3/C51:10 | C55:5/C56:12 | C59:1/C60:8/C61:15 |
| C46:6 | C50:2/C51:9 | C55:4/C56:11 | C59:0/C60:7/C61:14 |
| C46:5 | C50:1/C51:8 | C55:3/C56:10 | C60:6/C61:13 |
| C46:4 | C50:0/C51:7 | C55:2/C56:9 | C60:5/C61:12 |
| C46:3 | C51:6 | C55:1/C56:8 | C60:4/C61:11 |
| C46:2 | C51:5 | C55:0/C56:7 | C60:3/C61:10 |
| C46:1/C47:8 | C51:4/C52:11 | C56:6 | C60:2/C61:9 |
| C46:0/C47:7 | C51:2/C52:9 | C56:5/C57:12 | C60:1/C61:8/C62:15 |
| C47:6 | C51:1/C52:8 | C56:4/C57:11 | C60:0/C61:7/C62:14 |
| C47:5 | C51:0/C52:7 | C56:3/C57:10 | C61:6/C62:13 |
| C47:4 | C52:6 | C56:2/C57:9 | C61:5/C62:12 |
| C47:3 | C52:5 | C56:1/C57:8 | C61:4/C62:11 |
| C47:2/C48:9 | C52:4/C53:11 | C56:0/C57:7/C58:14 | C61:3/C62:10 |
| C47:1/C48:8 | C52:3/C53:10 | C57:6/C58:13 | C61:2/C62:9 |
| C47:0/C48:7 | C52:2/C53:9 | C57:5/C58:12 | C61:1/C62:8/C63:15 |

TABLE 11-continued

Exemplary triacylglyceride species.
GLYCEROLIPIDS
Triacylglyceride

| | | | |
|---|---|---|---|
| C48:6 | C52:1/C53:8 | C57:4/C58:11 | C61:0/C62:7/C63:14 |
| C48:5 | C52:0/C53:7 | C57:3/C58:10 | C62:6/C63:13 |
| C48:4 | C53:6 | C57:2/C58:9 | C62:5/C63:12 |
| C48:3 | C53:5/C54:12 | C57:1/C58:8 | |
| C48:2/C49:9 | C53:4/C54:11 | C57:0/C58:7/C59:14 | |
| C48:1/C49:8 | C53:3/C54:10 | C58:6/C59:13 | |

TABLE 12

Exemplary free fatty acid species.
FATTY ACYLS
Free fatty acid

| | |
|---|---|
| 14:1 | 20:2 |
| 14:0 | 20:1 |
| 15:1 | 20:0 |
| 15:0 | 21:4 |
| 16:2 | 21:3 |
| 16:1 | 21:2 |
| 16:0 | 21:1 |
| 17:2 | 21:0 |
| 17:1 | 22:6 |
| 17:0 | 22:5 |
| 18:3 | 22:4 |
| 18:2 | 22:3 |
| 18:1 | 22:2 |
| 18:0 | 22:1 |
| 19:3 | 22:0 |
| 19:2 | 24:5 |
| 19:1 | 24:4 |
| 19:0 | 24:3 |
| 20:5 | 24:2 |
| 20:4 | 24:1 |
| 20:3 | 24:0 |

TABLE 13

Exemplary acyl-COA species.
Metabolites
Acyl-CoA

| | |
|---|---|
| 17:0 | 18:1 |
| 2:0 | 18:0 |
| 3:0 | 20:4 |
| 4:0 | 20:3 |
| 6:0 | 20:2 |
| 8:0 | 20:1 |
| 10:0 | 20:0 |
| 12:0 | 22:6 |
| 14:1 | 22:5 |
| 14:0 | 22:4 |
| 16:1 | 22:3 |
| 16:0 | 22:2 |
| 18:3 | 22:1 |
| 18:2 | 22:0 |

TABLE 14

Exemplary acyl-carnitine species.
Metabolites
Acyl-carnitine

| | | |
|---|---|---|
| 12:0 | 14:2-OH | 22:0 |
| 2:0 | 14:1-OH | 22:6-OH |
| 4:1 | 14:0-OH | 22:5-OH |
| 4:0 | 16:3 | 22:4-OH |
| 6:1 | 16:2 | 22:3-OH |
| 6:0 | 16:1 | 22:2-OH |
| 8:3 | 16:0 | 22:1-OH |

TABLE 14-continued

Exemplary acyl-carnitine species.
Metabolites
Acyl-carnitine

| | | |
|---|---|---|
| 8:2 | 16:3-OH | 22:0-OH/24:6 |
| 8:1 | 16:2-OH | 24:5 |
| 8:0 | 16:1-OH | 24:4 |
| 8:3-OH | 16:0-OH | 24:3 |
| 8:2-OH | 18:3 | 24:2 |
| 8:1-OH | 18:2 | 24:1 |
| 8:0-OH | 18:1 | 24:0 |
| 10:3 | 18:0 | 24:6-OH |
| 10:2 | 18:3-OH | 24:5-OH |
| 10:1 | 18:2-OH | 24:4-OH |
| 10:0 | 18:1-OH | 24:3-OH |
| 10:3-OH | 18:0-OH | 24:2-OH |
| 10:2-OH | 20:4 | 24:1-OH |
| 10:1-OH | 20:3 | 24:0-OH/26:6 |
| 10:0-OH | 20:2 | 26:5 |
| 12:3 | 20:1 | 26:4 |
| 12:2 | 20:0 | 26:3 |
| 12:1 | 20:4-OH | 26:2 |
| 12:3-OH | 20:3-OH | 26:1 |
| 12:2-OH | 20:2-OH | 26:0 |
| 12:1-OH | 20:1-OH | 26:6-OH |
| 12:0-OH | 20:0-OH/22:6 | 26:5-OH |
| 14:3 | 22:5 | 26:4-OH |
| 14:2 | 22:4 | 26:3-OH |
| 14:1 | 22:3 | 26:2-OH |
| 14:0 | 22:2 | 26:1-OH |
| 14:3-OH | 22:1 | 26:0-OH |

TABLE 15

Exemplary ceramide (d18:1) species.
SPHINGOLIPIDS
Ceramide (d18:1)

| | |
|---|---|
| N17:0 | OH_N22:0 |
| N15:0 | N24:2 |
| N16:0 | N24:1 |
| OH_N15:0 | N24:0 |
| N18:1 | OH_N23:0 |
| OH_N16:0/N18:0 | OH_N24:2 |
| N19:0 | OH_N24:1 |
| OH_N19:1/N20:0 | OH_N24:0 |
| N21:0 | N26:1 |
| N22:2 | N26:0 |
| N22:1 | OH_N25:0 |
| N22:0 | N28:2 |
| N23:1 | N28:1 |
| N23:0 | N28:0 |

TABLE 16

Exemplary ceramide (d18:0) species.
SPHINGOLIPIDS
Ceramide (d18:0)

| | |
|---|---|
| N15:0 | N24:2 |
| N16:0 | N24:1 |
| OH_N15:0 | N24:0 |
| N18:1 | OH_N23:0 |
| OH_N16:0/N18:0 | OH_N24:2 |
| N19:0 | OH_N24:1 |
| OH_N19:1/N20:0 | OH_N24:0 |
| N21:0 | N26:1 |
| N22:2 | N26:0 |
| N22:1 | OH_N25:0 |
| N22:0 | N28:2 |
| N23:1 | N28:1 |
| N23:0 | N28:0 |
| OH_N22:0 | |

TABLE 17

Exemplary ceramide (d20:0) species.
SPHINGOLIPIDS
Ceramide (d20:0)

| | |
|---|---|
| N15:0 | N24:2 |
| N16:0 | N24:1 |
| OH_N15:0 | N24:0 |
| N18:1 | OH_N23:0 |
| OH_N16:0/N18:0 | OH_N24:2 |
| N19:0 | OH_N24:1 |
| OH_N19:1/N20:0 | OH_N24:0 |
| N21:0 | N26:1 |
| N22:2 | N26:0 |
| N22:1 | OH_N25:0 |
| N22:0 | N28:2 |
| N23:1 | N28:1 |
| N23:0 | N28:0 |
| OH_N22:0 | |

TABLE 18

Exemplary ceramide (d16:0) species.
SPHINGOLIPIDS
Ceramide (d16:0)

| | |
|---|---|
| N15:0 | N24:2 |
| N16:0 | N24:1 |
| OH_N15:0 | N24:0 |
| N18:1 | OH_N23:0 |
| OH_N16:0/N18:0 | OH_N24:2 |
| N19:0 | OH_N24:1 |
| OH_N19:1/N20:0 | OH_N24:0 |
| N21:0 | N26:1 |
| N22:2 | N26:0 |
| N22:1 | OH_N25:0 |
| N22:0 | N28:2 |
| N23:1 | N28:1 |
| N23:0 | N28:0 |
| OH_N22:0 | |

TABLE 19

Exemplary cerebroside species.
SPHINGOLIPIDS
Cerebroside

| | |
|---|---|
| N15:0 | N22:2 |
| OH_N12:0 | N22:1 |
| OH_N13:0 | N22:0 |
| OH_N14:0 | OH_N21:0 |
| N16:1 | OH_N22:2 |
| N16:0 | N23:0/OH_N22:1 |
| OH_N15:0 | OH_N22:0 |
| OH_N16:1 | N24:2 |
| OH_N16:0 | N24:1 |
| N18:1 | N24:0 |
| N18:0 | OH_N23:0 |
| OH_N17:0 | N25:1/OH_N24:2 |
| OH_N18:1 | OH_N24:1/N25:0 |
| OH_N18:0 | OH_N24:0 |
| N20:1 | N26:1 |
| N20:0 | OH_N25:1/N26:0 |
| OH_N19:0 | OH_N25:0 |
| OH_N20:1 | OH_N26:1 |
| OH_N20:0 | OH_N26:0 |

TABLE 20

Exemplary sulfatide species.
SPHINGOLIPIDS
Sulfatide

| | |
|---|---|
| N16:0 | N22:0 |
| N14:0 | OH_N22:2 |

TABLE 20-continued

Exemplary sulfatide species.
SPHINGOLIPIDS
Sulfatide

| | |
|---|---|
| OH_N14:0 | N23:0/OH_N22:1 |
| OH_N16:0 | OH_N22:0 |
| N18:1 | N24:2 |
| N18:0 | N24:1 |
| OH_N18:1 | N24:0 |
| OH_N18:0 | N25:1/OH_N24:2 |
| N20:1 | N25:0/OH_N24:1 |
| N20:0 | OH_N24:0 |
| OH_N20:1 | N26:1 |
| OH_N20:0 | N26:0 |
| N22:2 | OH_N26:1 |
| N22:1 | OH_N26:0 |

TABLE 21

Exemplary sphingomyelin species.
SPHINGOLIPIDS
Sphingomyelin

| | |
|---|---|
| N12:0 | N20:1 |
| N15:2 | N20:0 |
| N15:1 | N21:1 |
| N15:0 | N21:0 |
| N16:1 | N22:2 |
| N16:0 | N22:1 |
| N17:1 | N22:0 |
| N17:0 | N23:1 |
| N18:2 | N23:0 |
| N18:1 | N24:2 |
| N18:0 | N24:1 |
| N19:1 | N24:0 |
| N19:0 | N25:1 |
| N20:2 | N25:0 |

TABLE 22

Exemplary lactosyl ceramide species.
SPHINGOLIPIDS
Lactosyl ceramide

| | |
|---|---|
| N15:0 | N24:2 |
| N16:0 | N24:1 |
| OH_N15:0 | N24:0 |
| N18:1 | OH_N23:0 |
| OH_16:0/N18:0 | OH_N24:2 |
| N19:0 | OH_N24:1 |
| OH_N19:1/N20:0 | OH_N24:0 |
| N21:0 | N26:1 |
| N22:2 | N26:0 |
| N22:1 | OH_N25:0 |
| N22:0 | N28:2 |
| N23:1 | N28:1 |
| N23:0 | N28:0 |
| OH_N22:0 | |

TABLE 23

Exemplary sphingolipid species.
SPHINGOLIPIDS
Other sphingolipids

Sphingosine(C16)
Sphingosine-1-phosphate
Sphinganine-1-phosphate
Sphingosine
Sphinganine
Psychosine
lyso-sphingomyelin

TABLE 24

Exemplary cholesterol and 24-hydroxycholesterol species.
STEROL LIPIDS
Cholesterol and 24-Hydroxycholesterol Cholesterol
24-Hydroxycholesterol

TABLE 25

Exemplary cholesteryl ester species.
STEROL LIPIDS
Cholesteryl ester

| | |
|---|---|
| 14:1 | 20:2 |
| 14:0 | 20:1 |
| 15:1 | 20:0 |
| 15:0 | 21:4 |
| 16:2 | 21:3 |
| 16:1 | 21:2 |
| 16:0 | 21:1 |
| 17:2 | 21:0 |
| 17:1 | 22:6 |
| 17:0 | 22:5 |
| 18:3 | 22:4 |
| 18:2 | 22:3 |
| 18:1 | 22:2 |
| 18:0 | 22:1 |
| 19:3 | 22:0 |
| 19:2 | 24:5 |
| 19:1 | 24:4 |
| 19:0 | 24:3 |
| 20:5 | 24:2 |
| 20:4 | 24:1 |
| 20:3 | 24:0 |

(b) Biological Samples

Biological samples suitable for lipid profiling include blood, plasma, cerebral spinal fluid (CSF), brain tissue, fractionated cells or cell lysates, a tissue biopsy, surgical specimen, and autopsy material. A skilled artisan will recognize that the use of each biological sample is associated with advantages and disadvantages and the appropriate biological sample type is dependent upon the intended use of the method. For example, while a blood or plasma sample can be obtained with little discomfort and risk, the lipids in the blood or plasma sample may be from other parts of the body. Using CSF allows the analysis of lipids directly linked to brain lipid metabolism, but samples taken using spinal tap are uncomfortable and include moderate risks. Likewise, brain tissue samples offer the most direct measurement of the brain lipid profile, but require very invasive methods to obtain the samples and are associated with very high risks (most brain tissue samples are taken post-mortem).

II. Methods of the Invention

An embodiment of the present invention includes a method for determining a lipid profile of a subject. In an additional embodiment, a method for detecting a disorder, or disease, is provided. An embodiment provides a method for monitoring the progression of a disorder or disease. Further, an embodiment provides a method of monitoring therapy response of a disease or disorder. The method includes extracting lipids from a biological sample, analyzing a biological sample by shotgun lipidomics and shotgun sphingolipidomics, quantifying the concentrations or levels of lipid classes and lipid molecular species within the biological sample, and compiling the quantitation data into a lipid profile for the subject.

Shotgun lipidomics methods are known in the art and described in the examples herein (Han, X., et al. (2006) Shotgun lipidomics of cardiolipin molecular species in lipid extracts of biological samples, *J Lipid Res* 47, 864-879; and Jiang, X., and Han, X. (2006) Characterization and direct quantitation of sphingoid base-1-phosphates from lipid extracts: A shotgun lipidomics approach, *J. Lipid Res.* 47, 1865-1873, both incorporated herein by reference). By way of example, a lipid sample may be extracted from a biological sample using any method known in the art such as chloroform-methanol based methods, isopropanol-hexane methods, the Bligh & Dyer lipid extraction method or a modified version thereof, or any combination thereof. Suitable modifications to the Bligh & Dyer method include treatment of crude lipid extracts with lithium methoxide followed by subsequent liquid-liquid extraction to remove generated free fatty acids, fatty acid methyl esters, cholesterol, and water-soluble components that may hinder the shotgun analysis of sphingolipidomes. Since sphingolipids are inert to the described base-treatment (FIG. 4A, 4B, and Example 1), the global analysis and accurate quantitation to assess low and even very low abundant sphingolipids is possible by using a modified Bligh & Dyer method.

Following lipid extraction, it may be beneficial to separate the lipids prior to mass spectrometric analysis. Methods for separating lipids are known in the art. Suitable methods include, but are not limited to, chromatography methods such as solid-phase extraction, high performance liquid chromatography (HPLC), normal-phase HPLC, or reverse-phase HPLC.

The resultant lipid extracts are then analyzed by mass spectrometric techniques commonly known in the art and detailed in Example 1 (Han, X., et al. (2004) Towards fingerprinting cellular lipidomes directly from biological samples by two-dimensional electrospray ionization mass spectrometry, *Anal. Biochem.* 330, 317-331 and incorporated herein by reference). A skilled artisan will appreciate there are several mass spectrometric techniques that may be utilized to create a lipid profile of a sample including, but not limited to, gas chromatography-mass spectrometry, electrospray ionization (ESI) mass spectrometry (ESI-MS) in the positive or negative modes, tandem ESI-MS, multi-dimensional mass spectrometry, and MALDI mass spectrometry by methods known in the art and described in the examples herein.

The lipid profile of a subject is obtained using shotgun lipidomic techniques that provide absolute quantitation of the individual concentrations of lipid classes and molecular species within a given sample. A skilled artisan will recognize that a lipid profile contains numerous data points that are best managed and stored in a computer readable form. The resultant lipid profile is a weighted function of the quantified lipidome. The weighted function is derived from linear regression analysis of experimental results comparing lipid profiles of healthy subjects versus those of diseased subjects. Each lipid molecular species is multiplied by a weighting constant and summed. The function may vary between 0 and 1 with about 0 being a healthy sample and about 1 being a diseased sample. Methods of calculating the resultant function are described in Example 9.

(a) Neurological Disorders

The invention provides methods of determining lipid profiles for the detection of a diseased state. Disorders, or diseased states, that may be detected by the methods of the invention include disorders that result in an alteration of lipid levels. Exemplary disorders may include neurological disorders, neurodegenerative-associated disorders, diabetes, obesity, vascular diseases, and atherosclerosis. An embodiment of the invention provides methods of detecting neurological disorders such as ataxia associated and dementia associated disorders as well as acute brain injury and neurodegenerative disorders. Exemplary disorders include, but are not limited to, Alzheimer's disease, Parkinson's disease, Multiple sclerosis, Huntington's disease, Amyotrophic Lateral Sclerosis, Asphasia, Bell's palsy, and Creutzfeldt-Jakob disease.

(b) Subjects

The methods of the present invention may be utilized for any mammalian subject. Such mammalian subjects include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific value (e.g., captive or free specimens of endangered species), or mammals which otherwise have value.

Definitions

The term "lipidome" refers to all lipid classes and lipid molecular species present in a sample. Lipids can be classified into eight major categories including fatty acyls, glycerolipids, glycerophospholipids, sphingolipids, sterol lipids, prenol lipids, saccharolipids, and polyketides. These categories are subdivided into classes and subclasses, representing the entire repertoire of lipid molecular species.

The term "lipid class" refers to a set of lipid molecular species with common structural or chemical properties.

The term "lipid molecular species" refers to all the molecular formulas and conformations within a lipid class.

The term "lipidomics" refers to the large-scale study of the pathways and networks of cellular lipids.

The term "lipid profile" refers to a report or summary of the state of the lipids detected in a sample.

EXAMPLES

The following examples illustrate various embodiments of the invention.

Example 1

Materials and Methods Used in Examples 2-13

Lipid sample preparation. Lipid samples for the analysis of the majority of lipid classes including all of the major phospholipid classes, most of the lysophospholipid classes, TG, diacylglycerol, monoacylglycerol, cholesterol, cholesterol esters, oxysterols, SM, sphingosine, ceramide, and lysoSM among others are extracted by using a modified Bligh and Dyer procedure (Bligh, E. G., and Dyer, W. J. (1959) A rapid method of total lipid extraction and purification, Can. J. Biochem. Physiol. 37, 911-917; Cheng, H., Guan, S., and Han, X. (2006) Abundance of triacylglycerols in ganglia and their depletion in diabetic mice: Implications for the role of altered triacylglycerols in diabetic neuropathy, J. Neurochem. 97, 1288-1300; and Jiang, X., Cheng, H., Yang, K., Gross, R. W., and Han, X. (2007) Alkaline methanolysis of lipid extracts extends shotgun lipidomics analyses to the low abundance regime of cellular sphingolipids, Anal. Biochem. 371, 135-145, each incorporated herein by reference). Briefly, a protein assay on each plasma sample was performed. After 500 µl of plasma from each plasma sample was transferred to a disposable culture borosilicate glass tube (16×100 mm), a premixed lipid solution, used as internal standards for quantitation, was added to each plasma sample based on its protein concentration. These internal standards included 14:0-14:0 GPSer, 15:0-15:0 GPGro, 16:1-16:1 GPEtn, 14:1-14:1 GPCho, D17:1 diacylglycerol, 17:1 monoacylgycerol, T17:1 TG, 14:0 lysoGPCho, 14:0 lysoGPEtn, N12:0 SM, N16:0 sulfatide, $d_4$-palmitic acid, $d_7$-cholesterol, N17:0 ceramide, 16:0 sphingosine analog, etc. Addition of these internal standards allowed the final quantified lipid content to be normalized to both the protein content or the plasma sample volume and allowed the elimination of a potential loss from the incomplete recovery. These internal standards were selected because they only represent cc 0.1% of the endogenous cellular lipid content as demonstrated by ESI/MS lipid analysis. To each individual plasma sample, 4 ml of $CHCl_3$/MeOH (1:1, v/v) and 1.6 ml of LiCl solution (50 mM) was added. The extraction mixtures were vortexed and centrifuged at 2,500 rpm for 5 minutes. The $CHCl_3$ layer of each extract mixture was carefully removed and saved. An additional 2 ml of $CHCl_3$ was added into the MeOH/aqueous layer of each test tube. After centrifugation, the $CHCl_3$ layer from each individual sample was combined and dried under a nitrogen stream. Each individual residue was then resuspended in 4 ml of $CHCl_3$/MeOH (1:1), back-extracted against 1.8 ml of LiCl aqueous solution (10 mM), and the extract was dried. Each individual residue was resuspended in 1 ml of $CHCl_3$ and filtered with a 0.2-pm PETE syringe filter. Finally, each individual residue was reconstituted with a volume of 1 ml/mg of protein (which was based on the original protein content of the samples as determined from protein assays) in 1:1 $CHCl_3$/MeOH. The lipid extracts are finally flushed with nitrogen, capped, and stored at −20° C. for ESI/MS analyses (typically conducted within one week). A portion of each individual lipid extract (approximately 100 µl) was treated with LiOMe and followed by being washed with hexane as described in Example 3. The treated lipid samples were used for the analysis of the sphingolipidome of each individual plasma sample. Another portion of each individual original lipid extract was washed with 2 ml of hexane twice to remove most of the non-polar lipids such as TG, cholesterol, and cholesterol esters that are very abundant in plasma lipid extracts and interfere with the quantitation of phospholipid classes. The residue lipid solution after washing was used for the analysis of phospholipids by using intrasource separation followed by employing multi-dimensional MS analysis. Lipid extracts for the analysis of S1P, DHS1P, and lysoGPA molecular species were similarly prepared to that as described above, but from 100 µl of each individual plasma sample an extraction was performed by replacing the LiCl solution with 5% of acetic acid solution.

Mass spectrometric analysis of plasma lipid extracts. A triple-quadrupole mass spectrometer (Thermo Electron TSQ Quantum Ultra) equipped with an electrospray ion source and Xcalibur system software was mainly utilized. The first and third quadrupoles served as independent mass analyzers using a mass resolution setting of peak width 0.7, while the second quadrupole served as a collision cell for tandem mass spectrometry. The tandem mass spectrometry in the neutral loss (NL) mode was performed through coordinately scanning both the first and third quadrupoles with a mass difference (i.e., neutral loss) while collision activation was performed in the second quadrupole. The tandem mass spectrometry in the precursor-ion (PI) mode was performed through scanning the first quadrupole in the interested mass range and monitoring the third quadruple with an ion of interest while collision activation was performed in the second quadrupole.

Each lipid extract solution prepared above was properly diluted prior to infusion to the mass spectrometer, thereby guaranteeing no lipid aggregation was formed during analysis and minimizing any effects of residual inorganic components carried over during lipid extraction on ion suppression and/or chemical noise. The diluted lipid extract was directly infused into the ESI source at a flow rate of 4 µl/min with a syringe pump. Typically, a 1-min period of signal averaging in the profile mode was employed for each survey scan. For tandem mass spectrometry, a collision gas pressure was set at 1.0 mTorr, but the collision energy varied with the classes of lipids. Typically, a 2-min period of signal averaging in the profile mode was employed for acquisition of each tandem MS spectrum. All the MS spectra and tandem MS spectra were automatically acquired by a customized sequence subroutine operated under Xcalibur software. Mass spectra in survey scanning mode is acquired after intrasource separation (e.g., FIG. 2). The individual molecular species corresponding to each of the ion peaks is identified using multi-dimensional MS through building block analyses. Identification of these building blocks was accomplished by two powerful tandem MS techniques (i.e., neutral loss (NL) scanning and precursor ion (PI) scanning) that monitor the specific loss of a neutral fragment or the yield of a fragment ion, respectively, each of which represents a specific building block.

Some building blocks, each of which specifically identifies the polar head group of a lipid class of interest and which are commonly used for identification and quantitation in shotgun lipidomics, include NL scanning of 183 u (phosphocholine) for GPCho and SM, NL scanning of 87 u (serine) for GPSer, PI scanning of m/z 241 (inositol phosphate) for GPIns, PI scanning of m/z 153 (glycerophosphate derivative) for all anionic phospholipids, PI scanning of m/z 97 (sulfate) for sulfatide, NL scanning of 162 u (monohexose) for GalCer, NL scanning of 256 u for ceramide containing sphingosine backbone and non-hydroxyacyl amide, etc. Individual GPEtn molecular species and low-abundant GPEtn molecular species (including lysoGPEtn) were quantitated or refined after derivatization with Fmoc chloride.

Quantitation of individual lipid molecular species with a two-step procedure. First, the abundant and non-overlapping molecular species of a lipid class shown in one of the survey scans (e.g., FIG. 2) were quantified by comparison with a pre-selected internal standard (see above for examples) of the class after 13C de-isotoping. Next, some or all of the determined molecular species of the class (plus the pre-selected internal standard) were used as standards to determine the mass content of other low-abundance or overlapping molecular species using one or multiple tandem mass traces (each of which represents a specific building block of the class of interest) by two-dimensional MS. Moreover, several lipid classes such as GPEtn, cardiolipin, and TG, each of which sensitive building blocks were lacking, were quantitated by using the specialized shotgun lipidomics approach to quantitate the molecular species of these classes. For example, the neutral loss of Fmoc moiety from the tagged GPEtn molecular species in the negative-ion mode was very sensitive, showing over a 15.000-fold linear dynamic range, which was used to quantitate GPEtn and lysoGPEtn molecular species. Plasma cardiolipin molecular species were identified and quantified by an enhanced shotgun lipidomics approach by using a QqTOF mass spectrometer (QStar, Applied Biosystems/Sciex). Furthermore, a two-dimensional MS array analysis of TG molecular species (in which there is no head group present) based on neutral loss scanning of the three fatty acyl chain was used to assess the mass levels of plasma TG and diacylglycerol molecular species.

Data processing and bioinformatics. Shotgun lipidomics generates massive amounts of data that is challenging to analyze. The data from shotgun lipidomics analyses (including ion peak selection, baseline correction, data transferring, 13C-de-isotoping, peak intensity comparisons, and content level calculations) were analyzed using Microsoft Excel macros as described in Han, X. et al. (2004) Towards fingerprinting cellular lipidomes directly from biological samples by two-dimensional electrospray ionization mass spectrometry. Anal. Biochem. 330, 317-331 and incorporated herein by reference. Moreover, comparison of data sets between cases or data between control and disease states were performed by using stepwise multivariate regression analysis.

Example 2

Shotgun Lipidomics Measurements Indicated that Plasmalogen and Sulfatide are Depleted, and Ceramide is Enhanced, in the Earliest Recognizable Stage of Alzheimer's Disease Plasmalogen is a subclass of GPEtn that is highly enriched in both gray and white matter. Exploiting the power of shotgun lipidomics, it was demonstrated that there was a dramatic decrease in ethanolamine plasmalogen content present in white matter at the very mild stage of AD and a correlation of the deficiency in plasmalogen content in gray matter with AD severity (i.e., −10 mol % of depletion at the very mild stage of AD to −30 mol % reduction at the very severe stage of AD).

It was also demonstrated, using shotgun lipidomics, that sulfatide (a class of specialized myelin sphingolipids) was almost entirely depleted in grey matter (FIG. 3) and depleted up to 50% in white matter in very mild AD cases in comparison to age-matched controls in all examined brain regions. In order to determine whether this sulfatide depletion is specific to AD, post-mortem samples from patients with non-AD-related Parkinson's disease (PD) and non-PD related dementia with Lewy bodies (DLB) were assessed for sulfatide mass levels using shotgun lipidomics. In contrast to AD cases, the sulfatide mass levels of all examined brain regions in both gray and white matter from PD subjects were dramatically elevated compared to cognitively normal controls whereas the sulfatide mass levels on both gray matter and white matter in DLB were similar to those observed in controls. These studies suggest that sulfatide deficiency in very mild AD is specific among examined neurodegenerative diseases. Using shotgun lipidomics, the sulfatide mass levels in the CSF of subjects who have been clinically identified at the very earliest stage of AD (Mini-Mental State Examination score, 26.4±0.72) were examined. A marked decline of approximately 40% in sulfatide mass in the CSF of AD subjects relative to cognitively normal controls was measured. These results indicate that sulfatide mass content in CSF is a potential biomarker for the early diagnosis of AD.

Figures 4A, 4B:
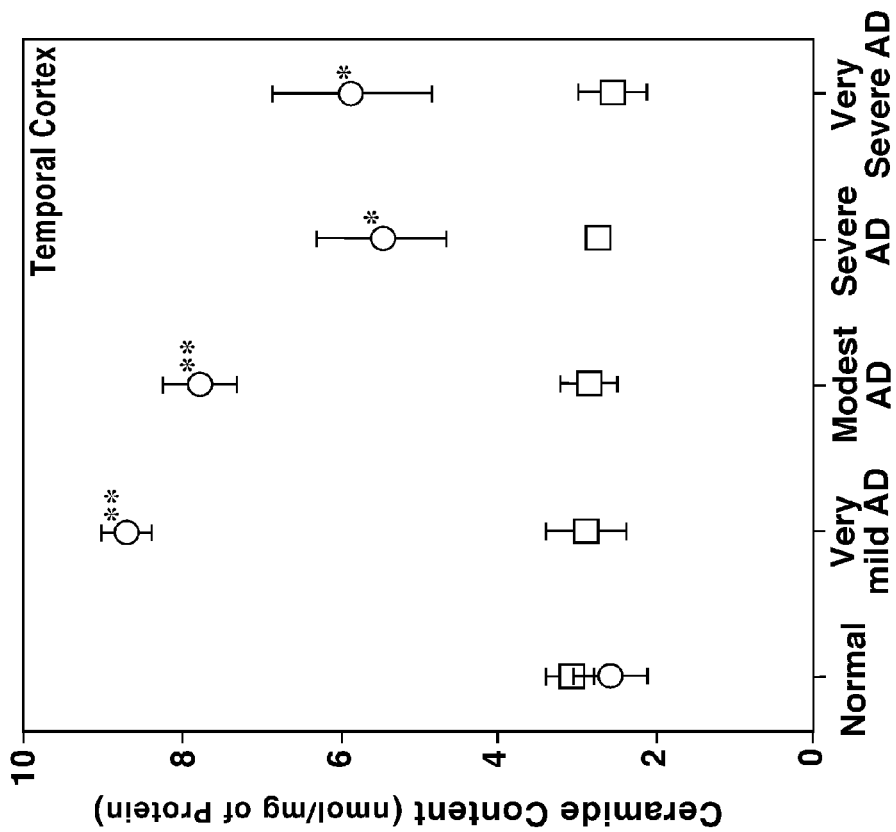
FIG. 4 shows the correlation of ceramide content in lipid extracts of gray and white matter of temporal cortex (FIG. 4A) and cerebellum (FIG. 4B) with the severity stages of AD dementia. The total content of ceramide molecular species in chloroform extracts of grey matter (square □ symbols) and white matter (circle ○ symbols) was quantitated using shotgun lipidomics. The data were normalized to the protein control of each tissue sample and are presented as the means±SEM from six separate subjects per group. Key: (*) denotes p<0.001 and (**) denotes p<0.0001 compared with controls. The SEM is represented by error bars.

Excessive ceramide has diverse biological consequences including up-regulation of cytokines, generation of reactive oxygen species, interruption of the mitochondrial respiratory chain, and introduction of apoptosis. Ceramide content measured in white matter using shotgun lipidomics showed a greater than three-fold elevation in AD subjects relative to cognitively normal controls (FIGS. 4A and 4B). In addition, there were substantial composition changes of ceramide molecular species in white matter of all examined regions from AD subjects with different degrees of AD severity.

The results indicated that most changes of sulfatide content occurred between the cognitively normal state and earliest clinically recognizable stage of AD. Only a small or no further loss of sulfatide was manifested at the advanced stages of AD (FIG. 3). Similarly, the maximal content of ceramide in white matter in all examined stages of AD occurred at the earliest clinically recognized stage of AD (FIGS. 4A and 4B). In contrast, no changes between very mild AD and control brain tissue samples were measured by shotgun lipidomics in the levels of other phospholipid and sphingolipid classes, including: GPCho, diacyl GPEtn (dGPEtn), GPIns, SM, Gal-Cer, glucosylceramide, GPGro, GPSer, free fatty acid, and cholesterol. Only modest alterations in the lipid masses of these other phospholipid and sphingolipid classes were found in severely demented AD cases.

Example 3

Figure 5:
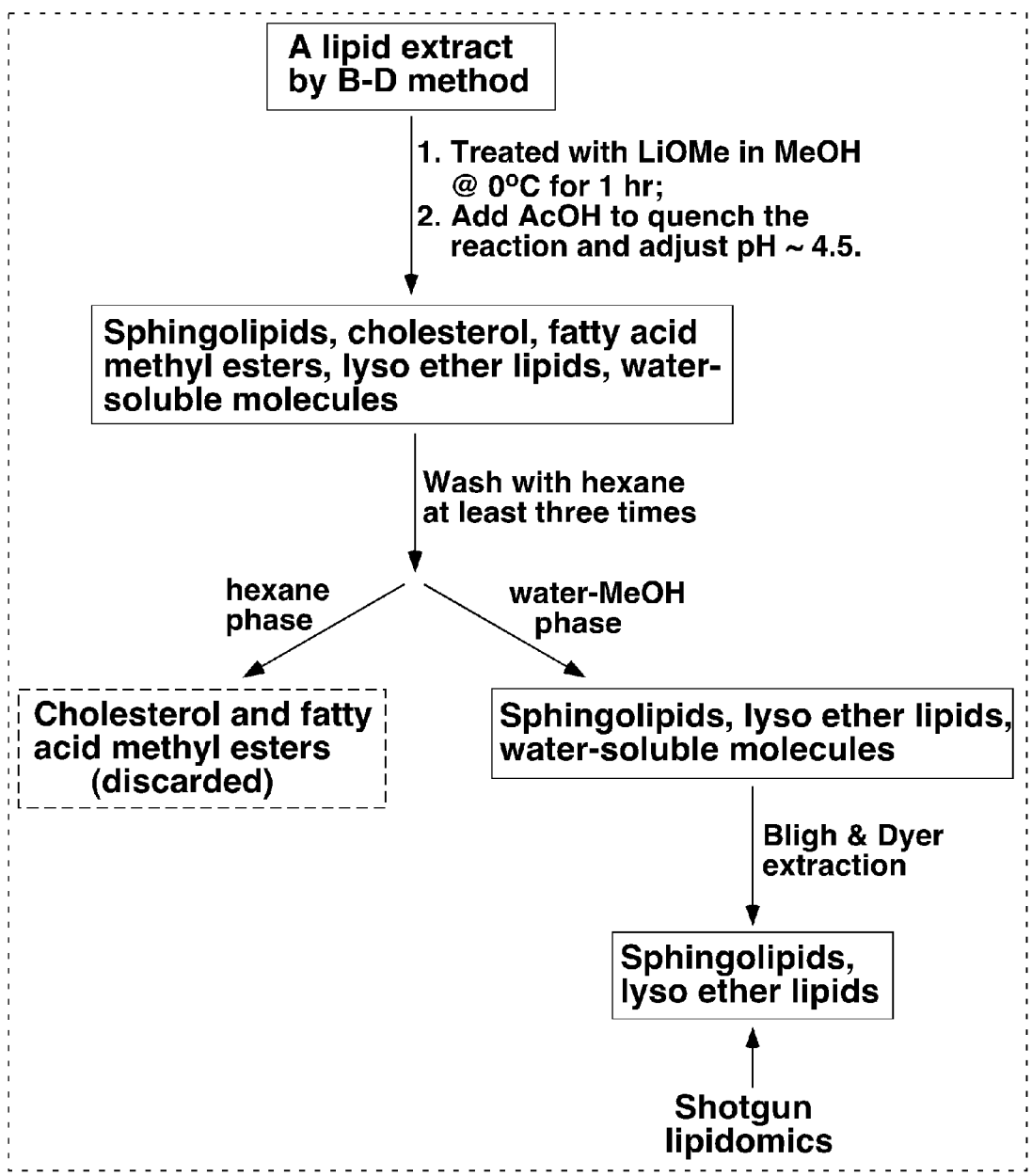
FIG. 5 is a schematic illustration of sample preparation for shotgun sphingolipidomics.
Figure 6A:
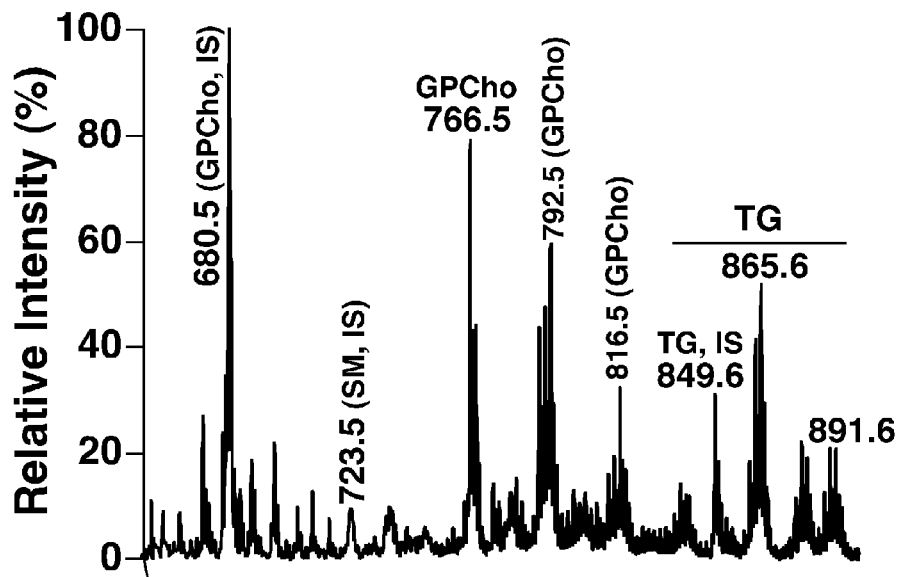
FIG. 6 presents the results of the shotgun lipidomics analysis of sphingolipid molecular species before and after treatment with LiOMe. The mass spectra were acquired directly from a lipid extract of human plasma before (FIGS. 6A and 6B) and after (FIGS. 6C and 6D) treatment with LiOMe as illustrated in FIG. 5. The mass spectra in FIG. 6A and FIG. 6C are the survey scans and the mass spectra in FIG. 6B and FIG. 6D are acquired from the neutral loss of 183.1u. IS denotes internal standard. The ion peaks in FIG. 6D represent lithiated SM molecular species. TG stands for triacylglycerol.
Figure 6B:
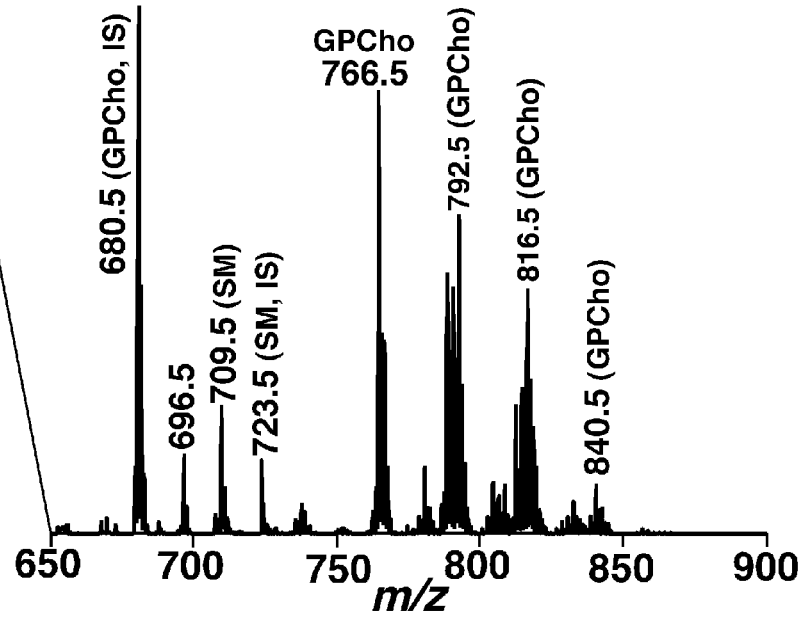
Figure 6C:
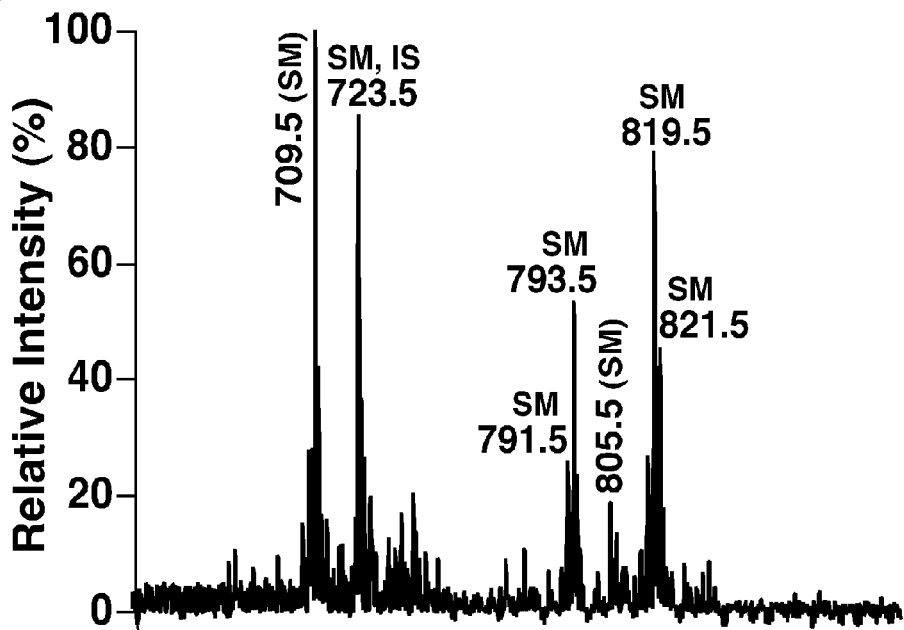
Figure 6D:
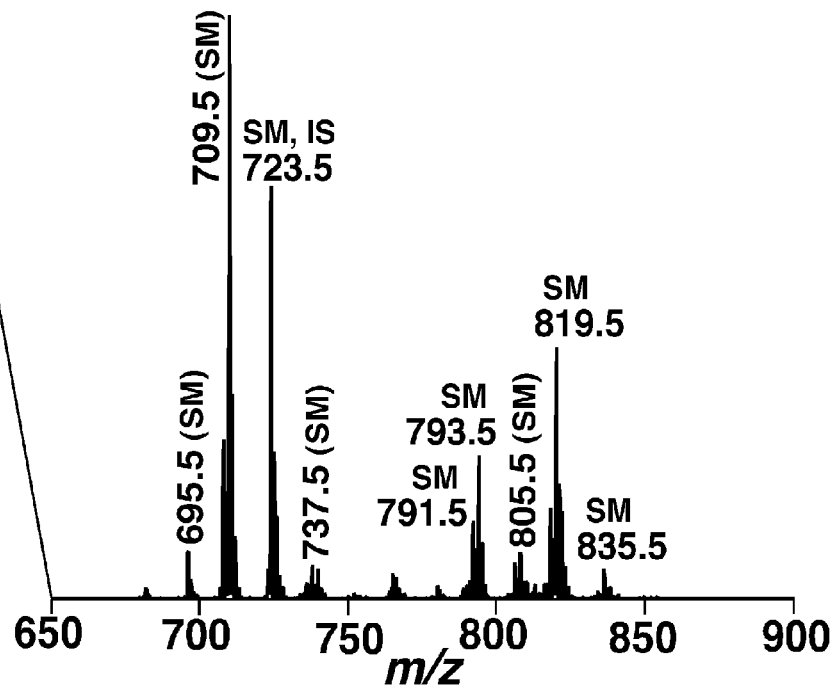

Special Lipid Sample Preparations for Sphingolipidomes Minimized Signal Overlap with Other Lipid Classes and Enhanced the Dynamic Range of Mass Spectral Analysis Shotgun lipidomics analysis of the sphingolipidome (i.e., all the sphingolipid molecular species present in a biological sample) may be hindered in some instances due to signal overlap during MS analysis with potential isobaric lipid molecular species in other lipid class(es), and by the limited dynamic range of the instrumentation employed for quantitation. The dynamic range is affected by the presence of other major lipids such as cholesterol and glycerolipids. These limitations to shotgun lipidomics analysis were overcome by the removal of cholesterol and glycerolipids (e.g., TG and phospholipids) through treatment of the crude lipid extracts with lithium methoxide (LiOMe) and subsequent liquid-liquid extraction to remove the generated free fatty acids, fatty acid methyl esters, cholesterol, and water-soluble components. Since sphingolipids are inert to this base treatment (see FIG. 5 for the detailed procedures), the global analysis and accurate quantitation to assess low and even very low abundant sphingolipids was achieved.

FIG. 6 shows comparisons of MS analysis of a lipid extract from human plasma before (FIGS. 6A and 6B) and after (FIGS. 6C and 6D) the treatment of the extract with LiOMe, along with the mass spectra using neutral loss scanning of 183.1 u, which is specific to GPCho and SM molecular species in the mass region. After treatment with LiOMe, many additional low abundance and/or overlapped SM molecular species were detected. In addition, this procedure enriched sphingolipids in the sample without the use of column chromatography, and increased the effective range of quantitation for sphingolipid molecular species since many of the co-existing lipids (glycerolipids, cholesterol, etc.) were eliminated. This approach established a procedure for the shotgun lipidomics analysis of many minor sphingolipid classes (e.g., ceramide-1-phosphate, sphingosine, lysoSM, etc.).

Example 4

The Content of Sphingosine-1-Phosphate and Dihydrosphingosine-1-Phosphate in Plasma from Subjects with Very Mild AD was Significantly Lower in Comparison to that in Controls S1P is an essential bioactive sphingolipid metabolite that has recently become the focus of intense interest. S1P functions are mediated by its binding to a family of 5 G protein-coupled receptors which are widely expressed and are thought to regulate important physiological actions (i.e., neuron survival). S1P may participate in various pathological conditions and serves as a second messenger which is important in the regulation of calcium homeostasis, cell growth, and suppression of apoptosis. DHS1P has been found to bind to S1P receptors as does S1P, but its binding ability is less potent.

Shotgun lipidomics were used to quantify the mass levels of S1P and DHS1P in biological samples with a linear dynamic range of over 100-fold and a detection limit at the concentration level of low pmol/µl by precursor scanning of m/z 79. Mass levels of sphingoid base-1-phosphates in plasma samples from 6 individuals with very mild AD and 6 age-matched cognitively-normal controls were measured (see FIG. 7) to be significantly different (444.1±86.3 µmol S1P and 215.3±22.1 µmol DHS1P per ml of plasma from AD patients vs. 686.0±41.4 µmol S1P and 301.5±33.5 µmol DHS1P per ml of plasma from controls, $p<0.05$, $n=6$).

Example 5

Figure 8A:
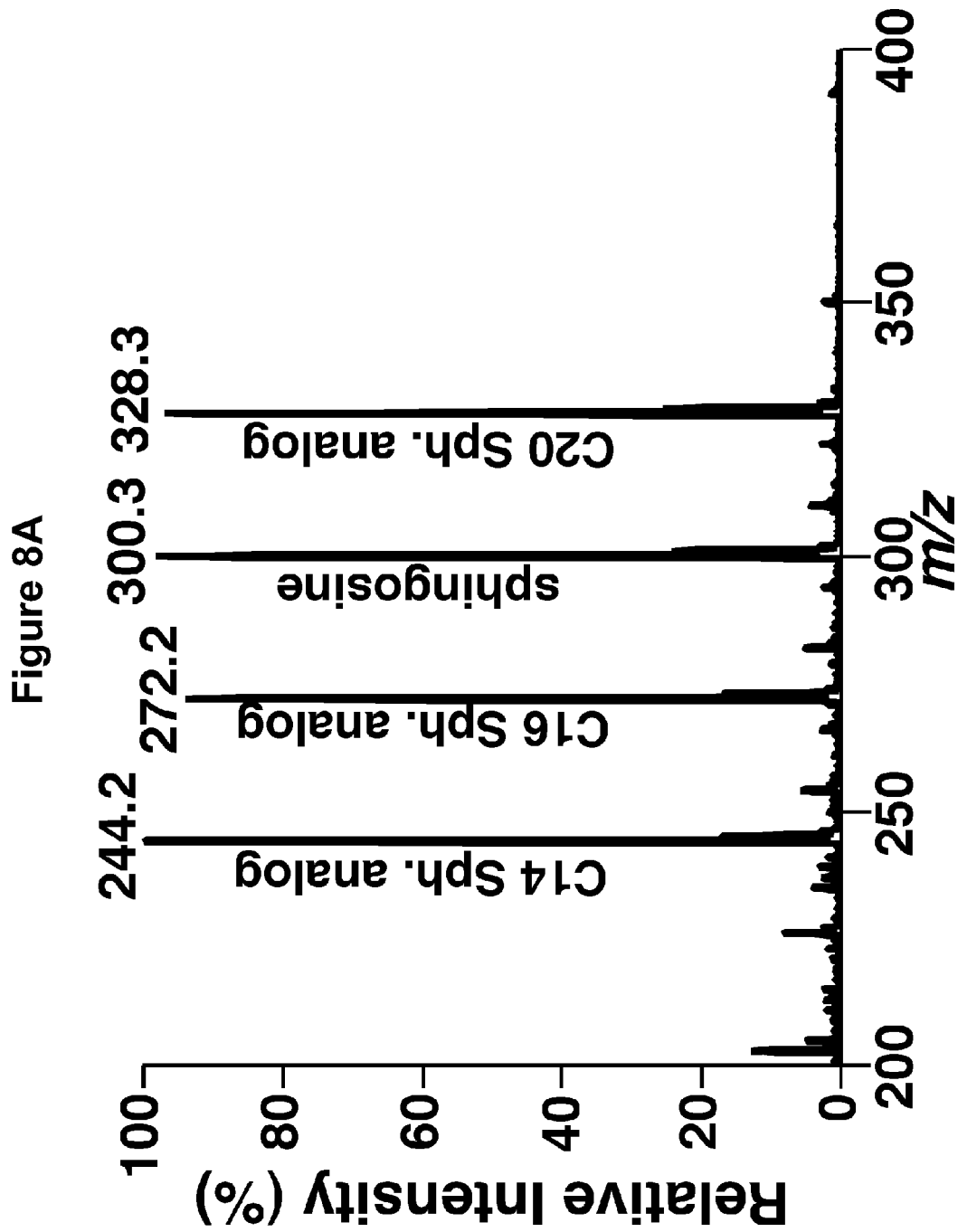
FIG. 8 presents the results of ESI/MS and MS/MS analyses of sphingosine and its analogs. ESI/MS analysis (FIG. 8A) of an equimolar mixture of sphingosine analogs (0.1 pmol/μl each in MeOH+0.2% acetic acid) was performed in the positive-ion mode. Product ion analysis of sphingosine (FIG. 8B) was performed after collision-induced disassociation. Tandem MS analyses of the equimolar mixture (FIG. 8C) and a lipid extract from 100 μl of plasma sample (FIG. 8D) were also performed using neutral-loss (NL) scanning 48 u (i.e., NL of a $H_2O$ and a $CH_2O$).
Figure 8B:
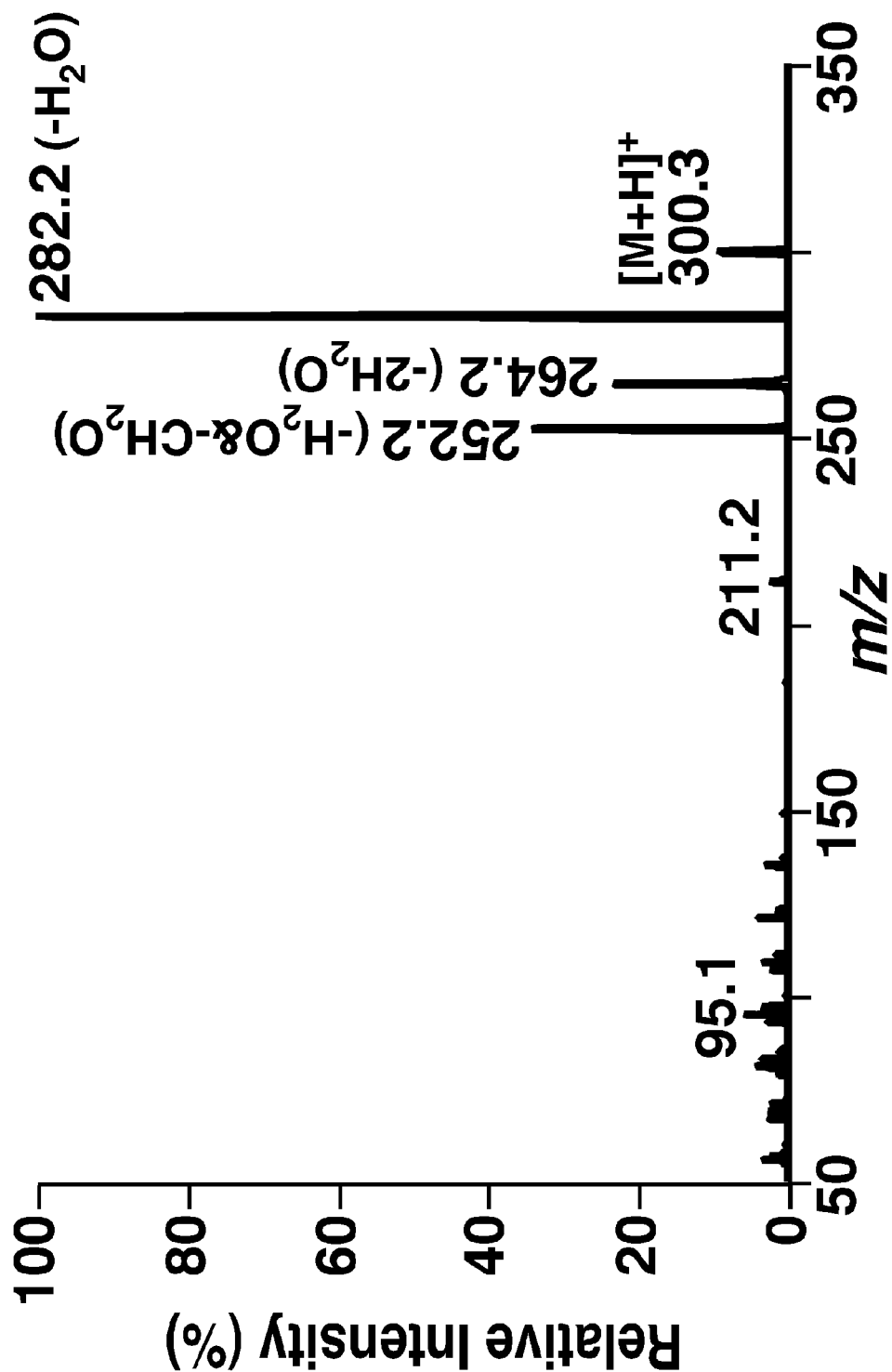
Figure 8C:
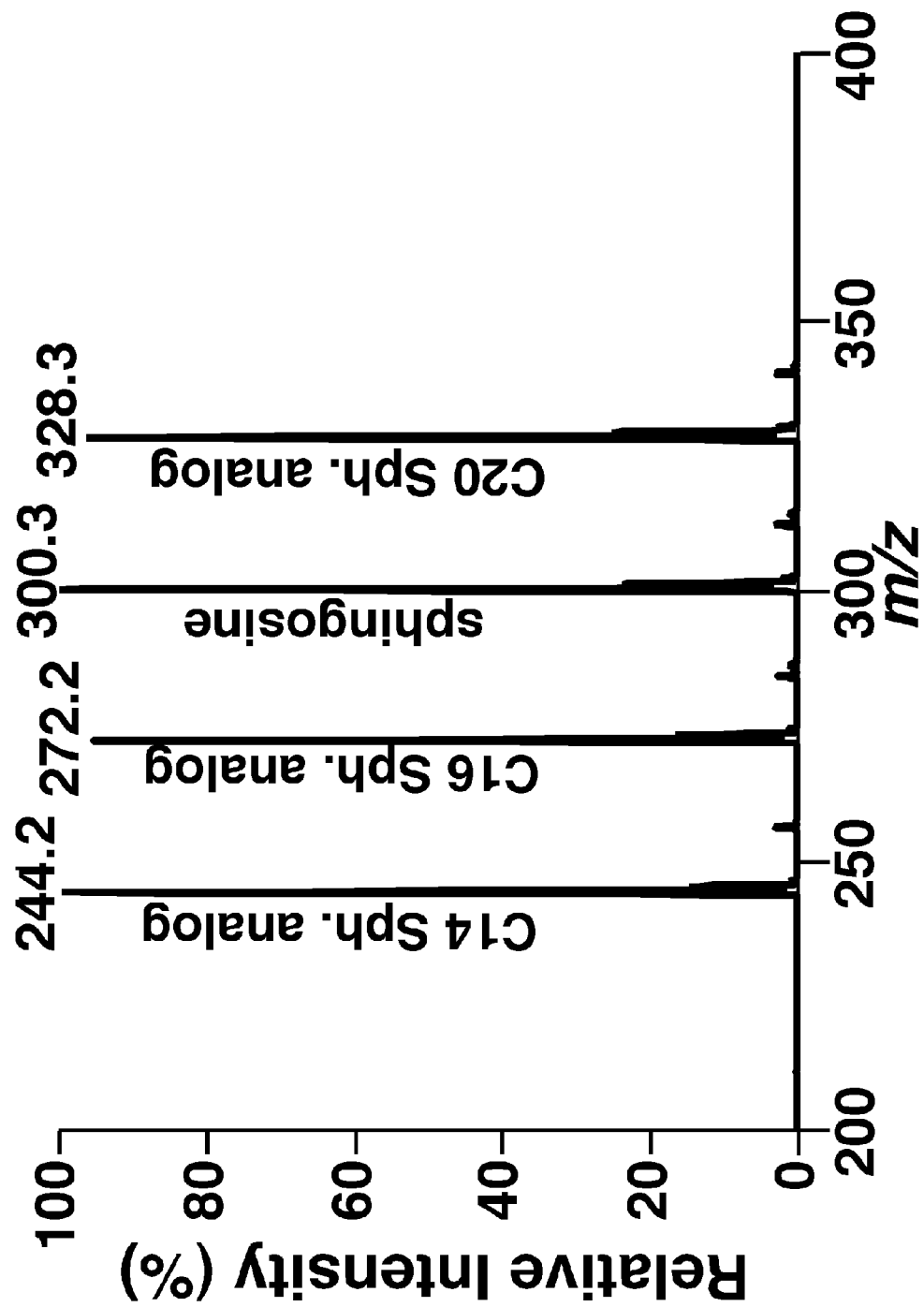
Figure 8D:
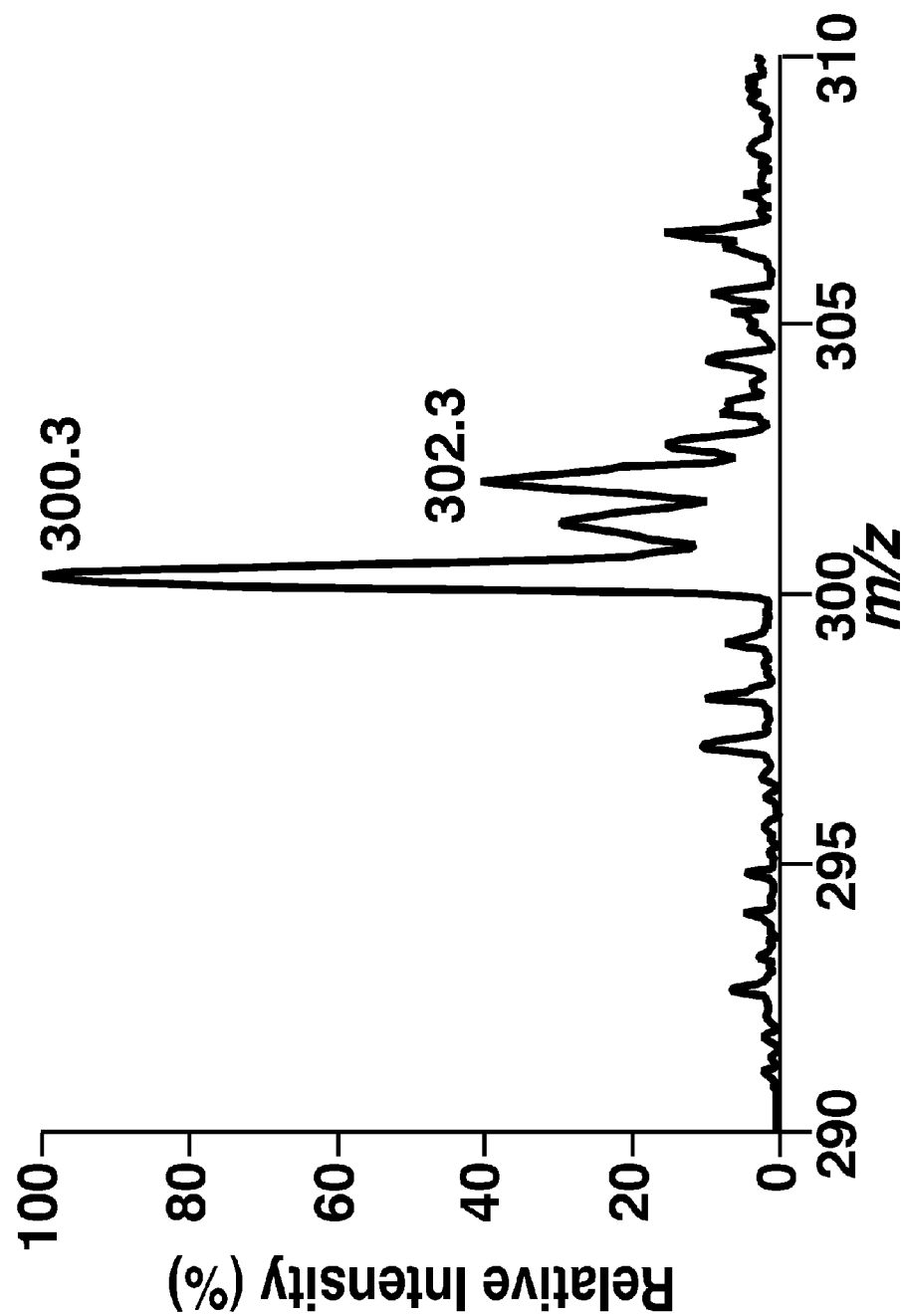

Shotgun Sphingolipidomics were Developed to Characterize and Quantify Sphingosine in Human Plasma Samples Sphingosine can be readily ionized in the positive-ion mode in the presence of a small amount of acetic acid (e.g., 0.2%) in MeOH (FIG. 8A). The ionization efficiencies of these protonated sphingosine analogs (e.g., C14 to C20) were essentially identical (within experimental error) after $^{13}$C deisotoping (FIG. 8A). Each of these analogs can be used as an internal standard for the quantitation of sphingosine. These sphingosine analogs can be readily fragmented after collision-induced dissociation (CID), and the CID mass spectra acquired using a low collision energy (e.g., 10 to 15 eV) showed an abundant and unique fragment, corresponding to the neutral loss of 48.0 u (i.e., a methylaldehyde molecule and a water molecule) with two predominant, non-specific water-loss fragments (FIG. 8B). The mass spectrum acquired using neutral-loss scanning of 48 u from an equimolar mixture of sphingosine analogs showed an essentially identical profile (FIG. 8C) to that acquired by the survey scan of the mixture (FIG. 8A). Direct profiling of a lipid extract from human plasma by using neutral loss of 48 u after treatment of the lipid extract with LiOMe followed by liquid-liquid extraction as described in Example 3 revealed two abundant ion peaks at m/z 300.3 and 302.3, corresponding to sphingosine and sphinganine (FIG. 8D).

Example 6

Figure 9:
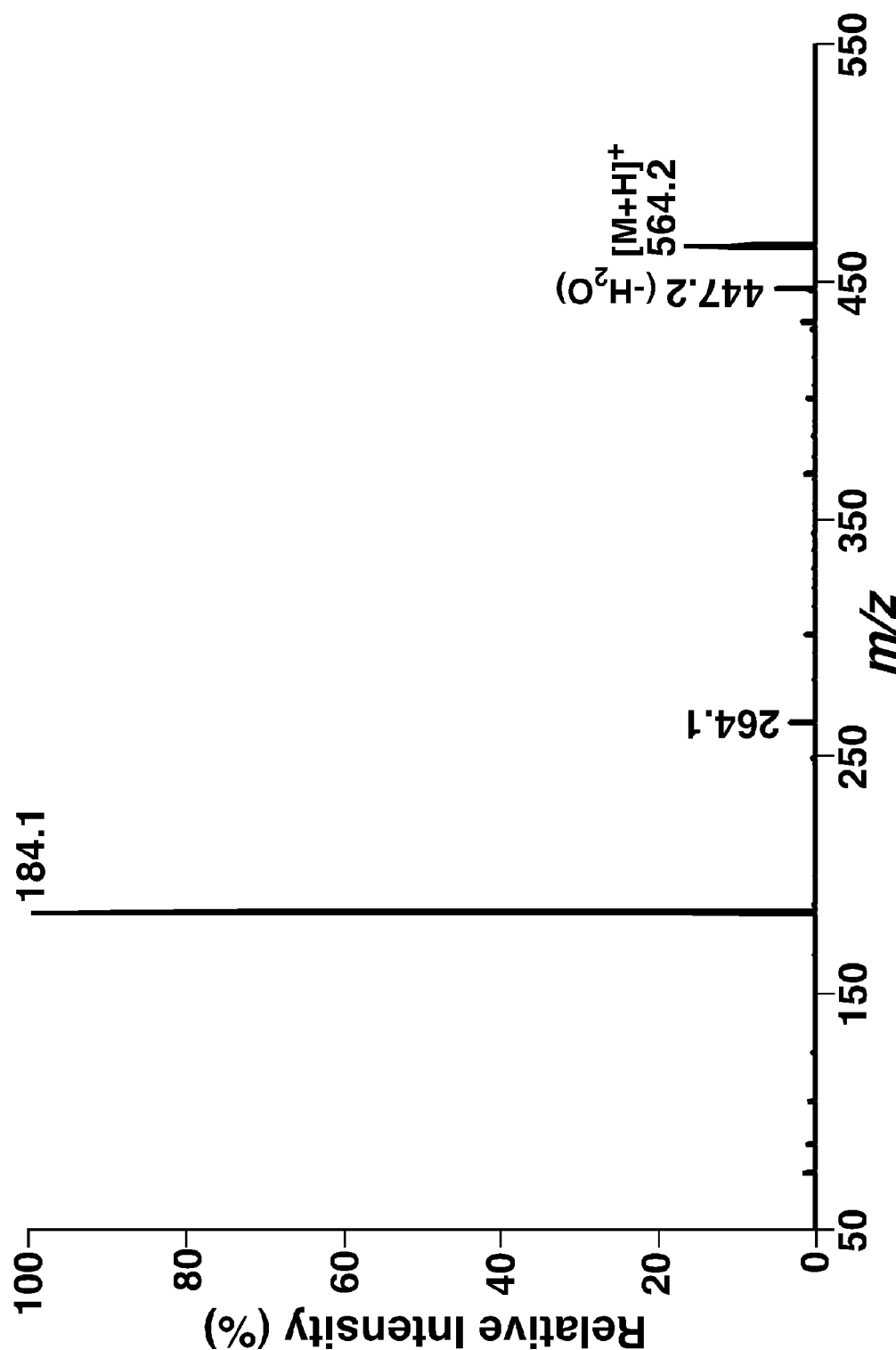
FIG. 9 shows the product-ion mass spectrum of lysosphingomyelin after collision-induced dissociation in the positive-ion mode.

Shotgun Sphingolipidomics were Developed to Characterize and Quantify Lysosphingomyelin in Human Plasma Samples Choline-containing phospholipids have been extensively studied previously by ESI/MS and can be readily ionized from their protonated, lithiated, or sodiated adducts. These adducts can be profiled by using precursor-ion scanning of m/z 184.1, or neutral loss scanning of 183.1 u, or neutral loss scanning of 59 u, respectively. For example, product ion analysis of protonated lysoSM shows a predominant fragment at m/z 184 (i.e., protonated phosphocholine) (FIG. 9). LysoSM molecular species were also detected in the lipid extracts of human plasma samples using precursor-ion scanning of m/z 184.1.

Example 7

The Levels of Plasmalogen Molecular Species in Plasma from Subjects with Very Mild AD were Significantly Lower than Those in Controls Using an improved shotgun lipidomics technique, the levels of GPEtn and lysoGPEtn in plasma lipid extracts from very mild AD patients and control individuals were compared. This improved technique exploited the facile neutral loss of the specifically tagged Fmoc moiety from amine-containing lipid molecular species after addition of Fmoc-CI prior to infusion of a diluted lipid extract into an ESI mass spectrometer. This technique dramatically improved the sensitivity, dynamic range, and detection limit for GPEtn and lysoGPEtn molecular species. Although GPEtn and lysoGPEtn are not the major lipid classes in the plasma lipidome, the individual molecular species of these lipid classes can be readily identified (FIG. 10).

Figure 10A:
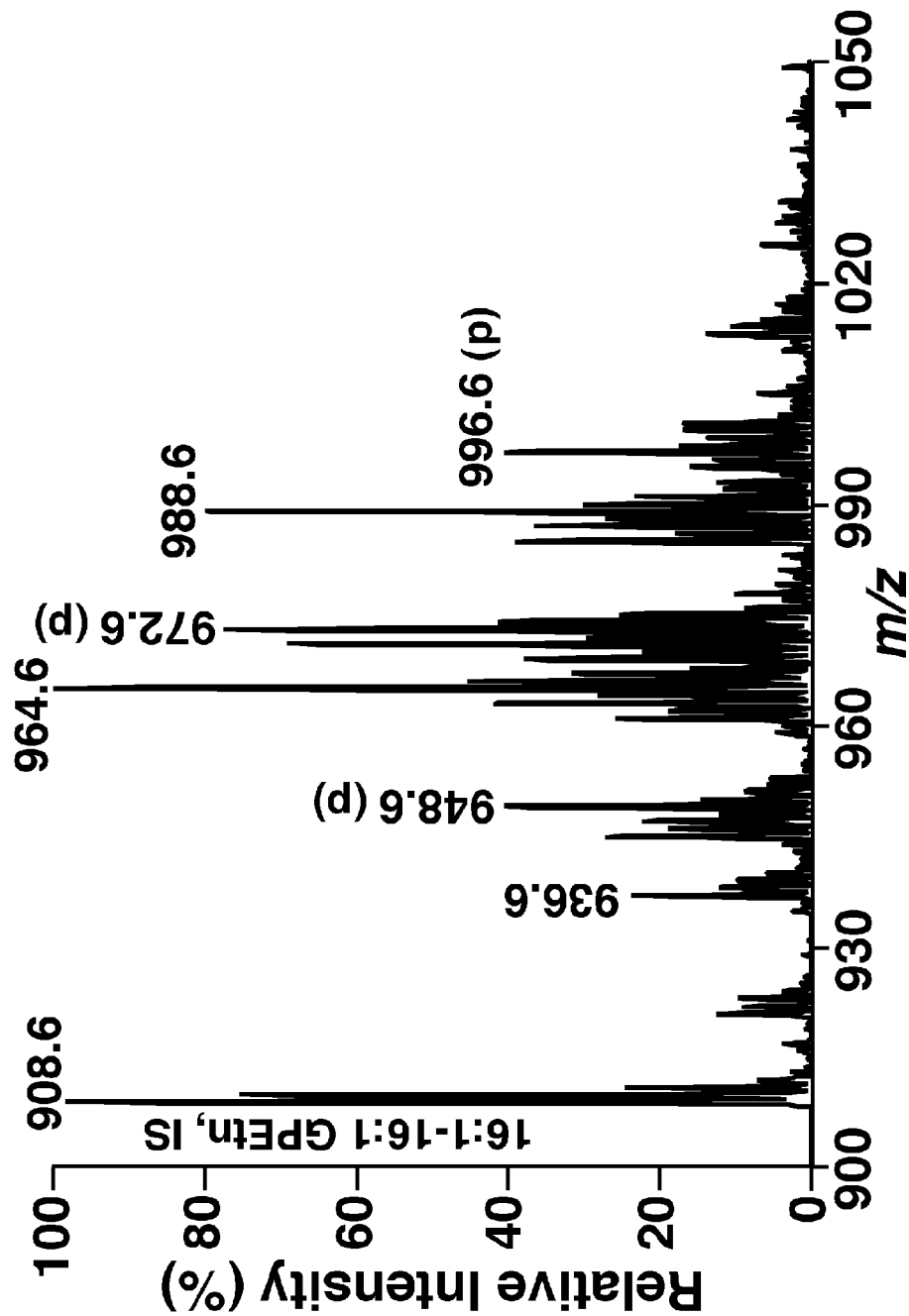
FIGS. 10A and 10C show the mass spectra of lipid extracts from control individuals and FIGS. 10B and 10D show the mass spectrometric analyses of lipid extracts from subjects with very mild AD.
Figure 10B:
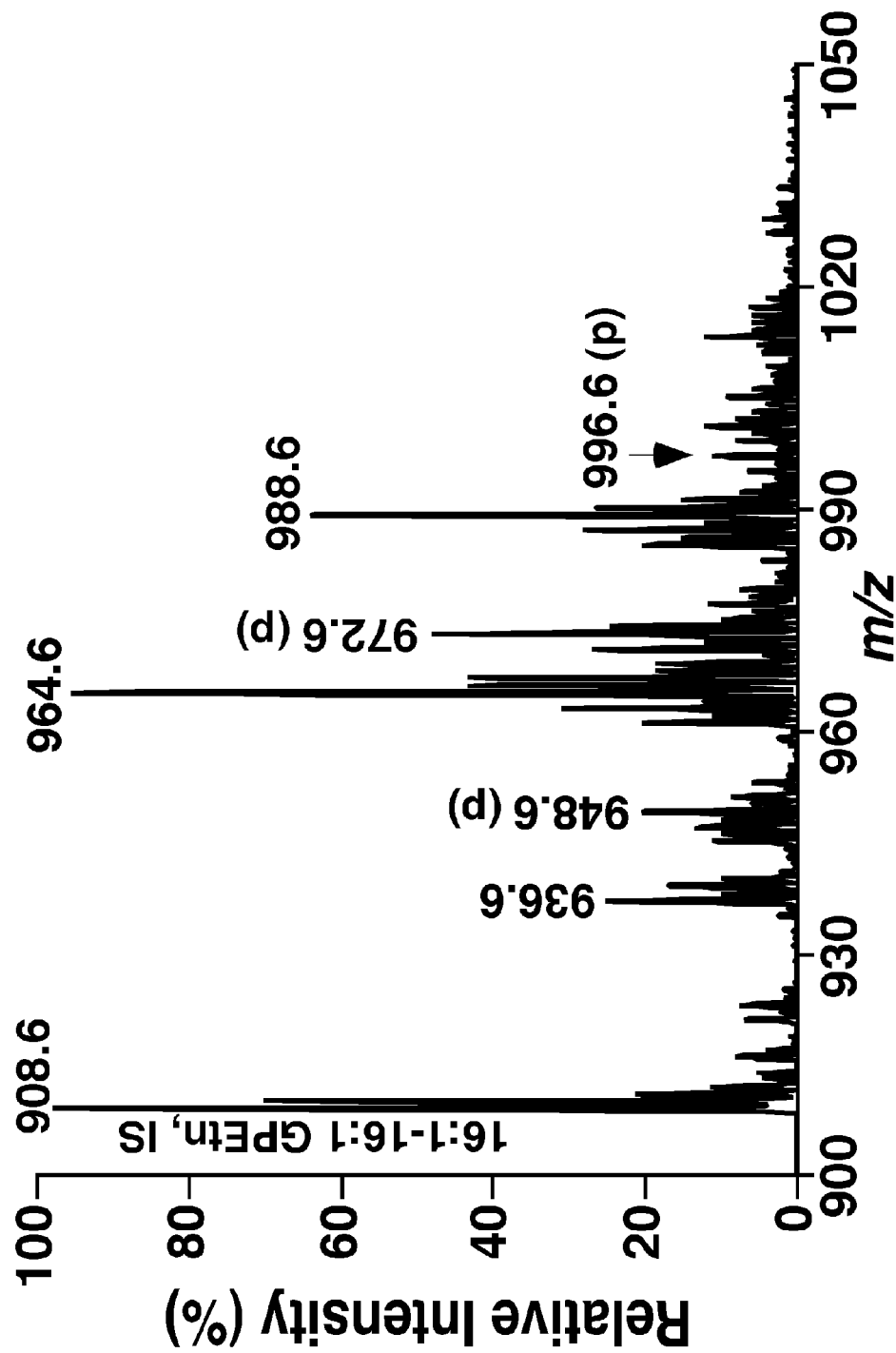
Figure 10C:
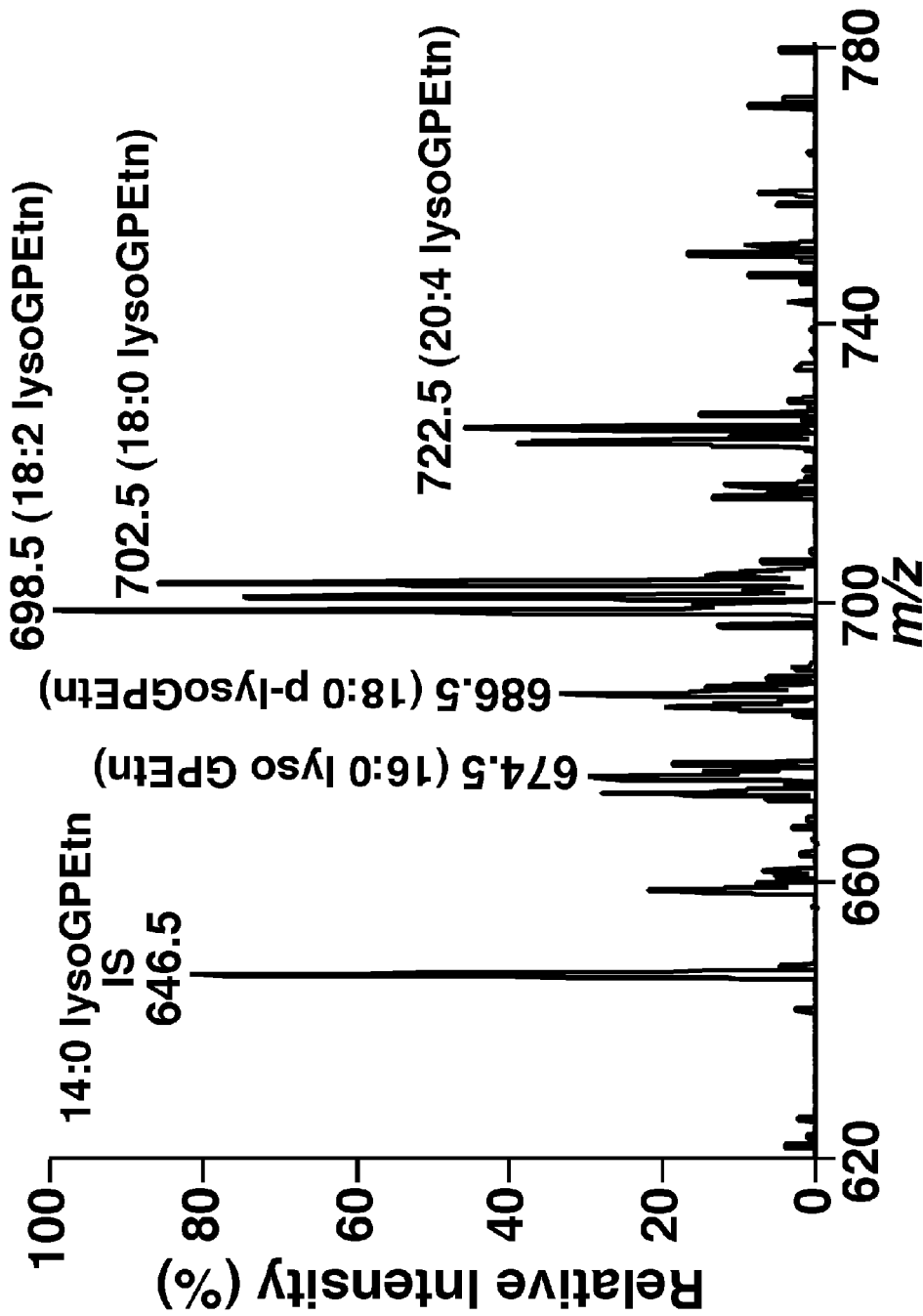
Figure 10D:
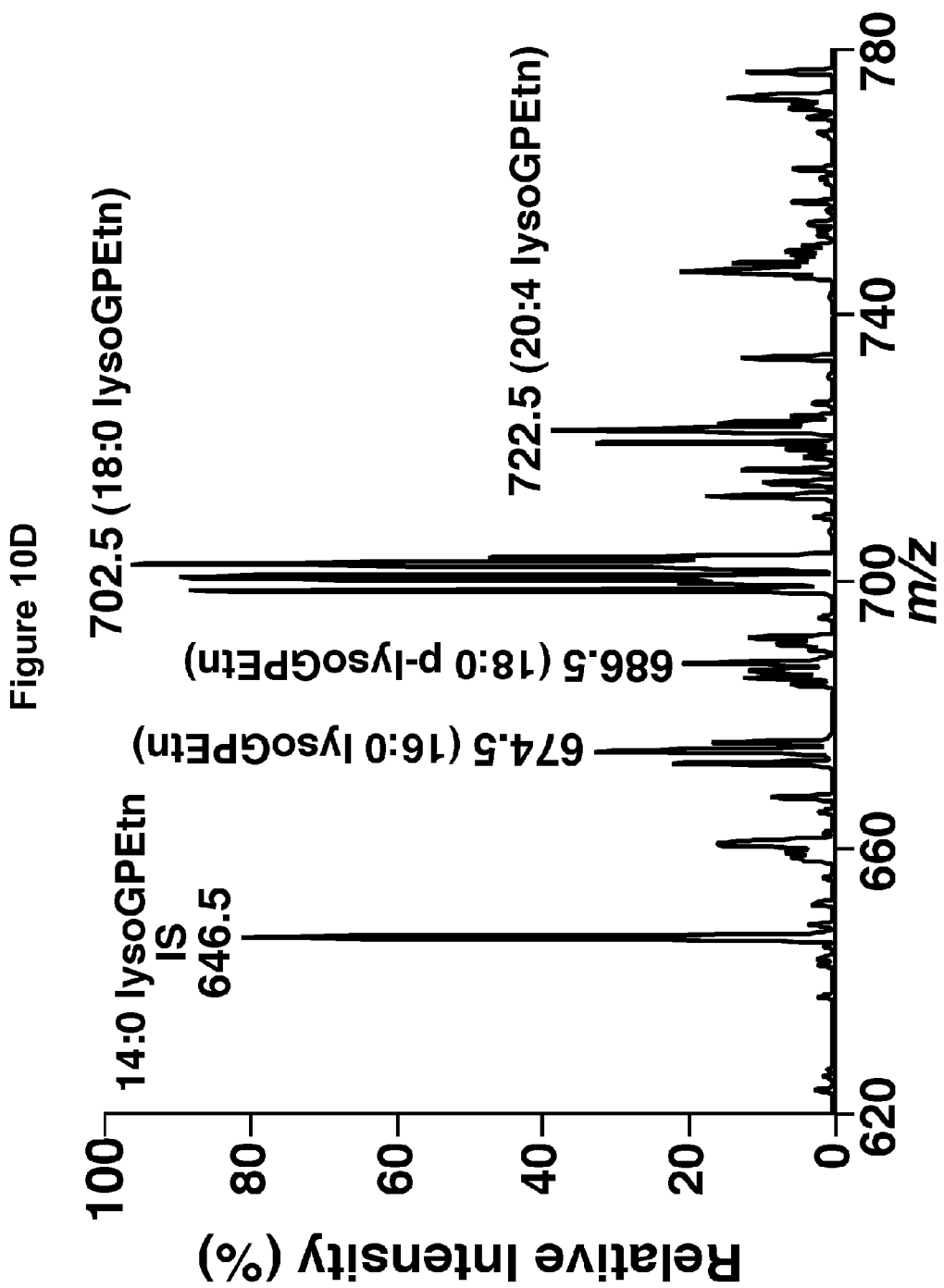
Figure 11A:
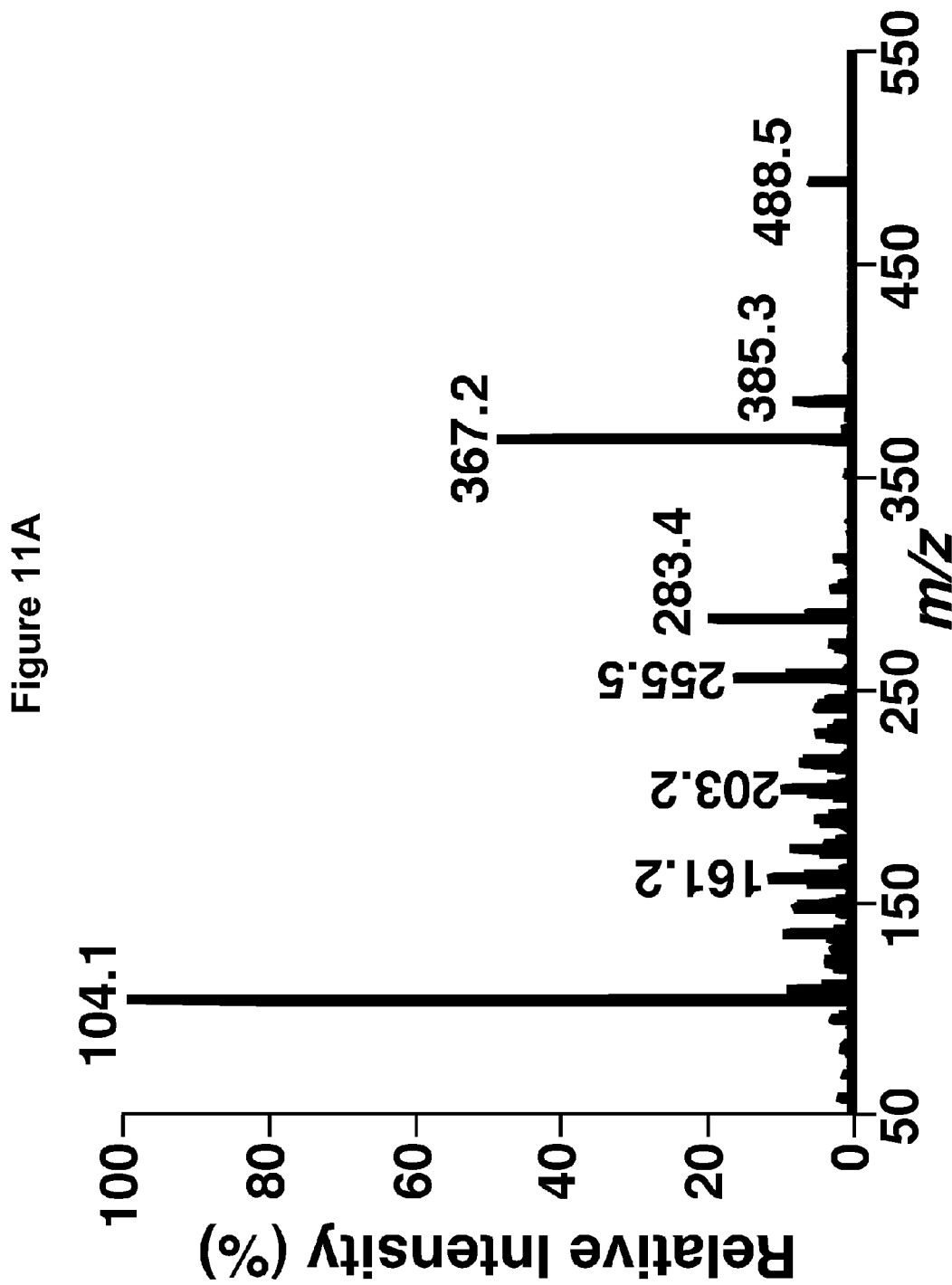
FIG. 11A represents tandem MS analyses of singly-charged 24S-OH-Chol.
Figure 11B:
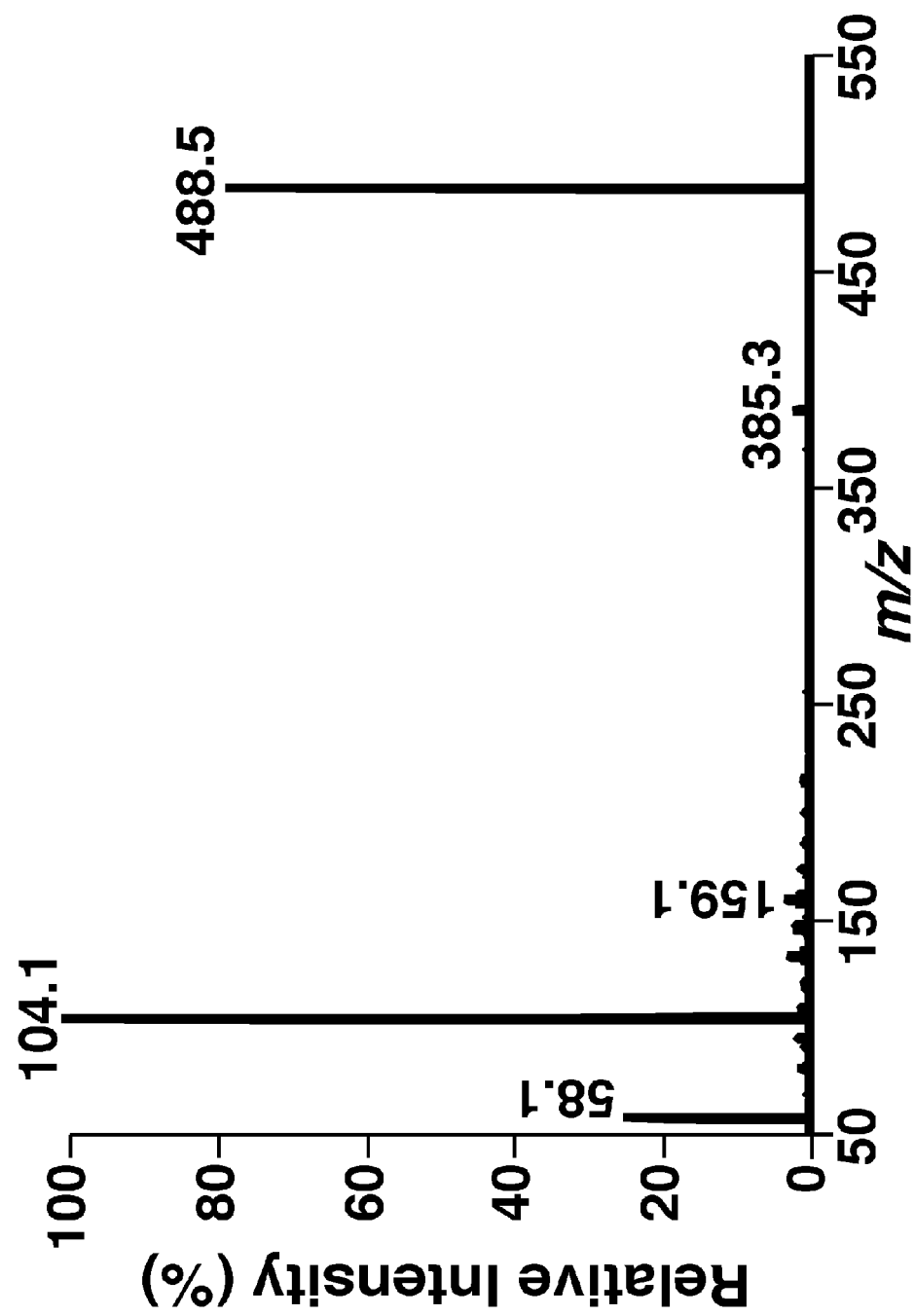
FIG. 11B represents singly-charged 27-OH-Chol.
Figure 11C:
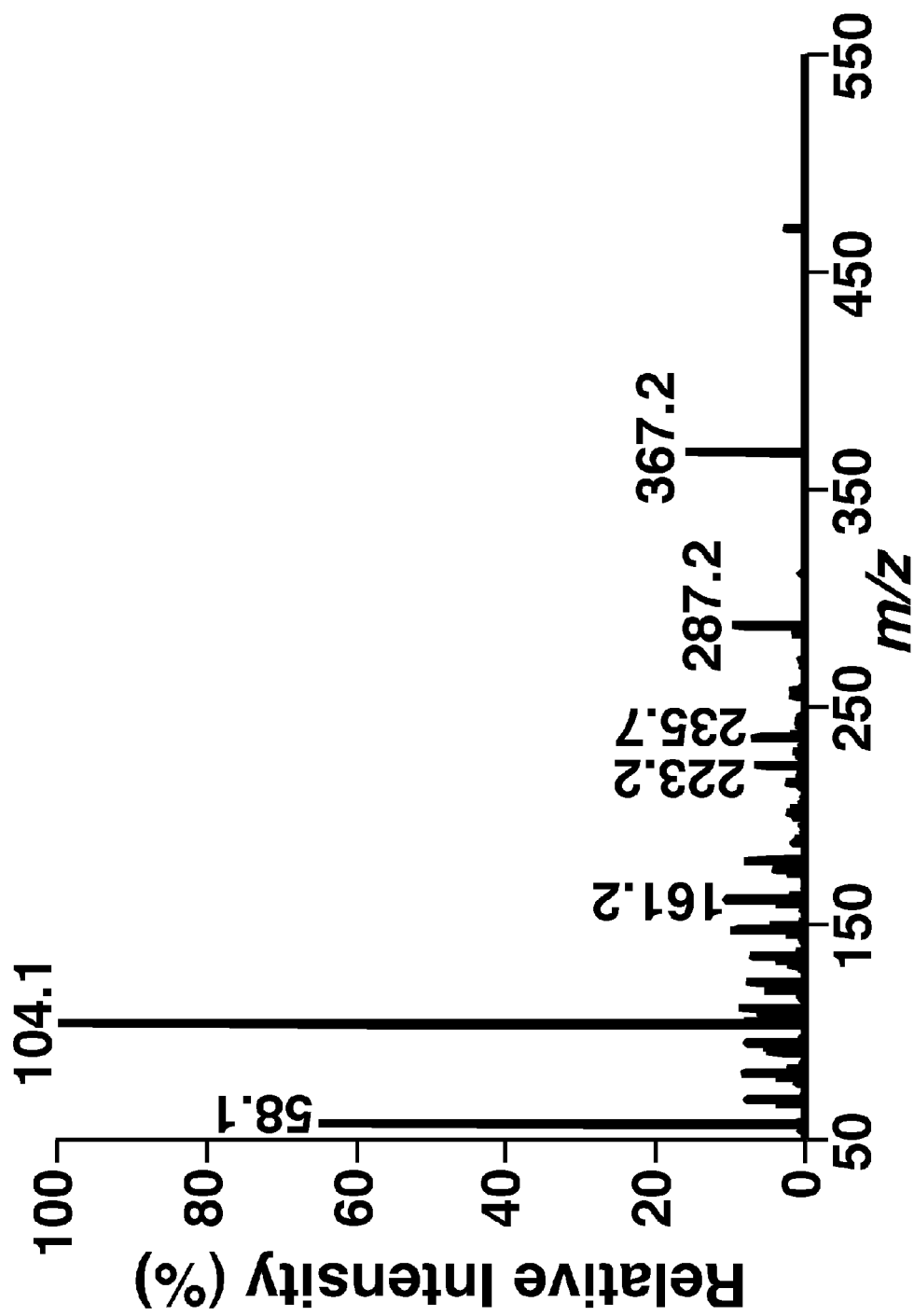
FIG. 11C represents doubly-charged 24S-OH-Chol.
Figure 11D:
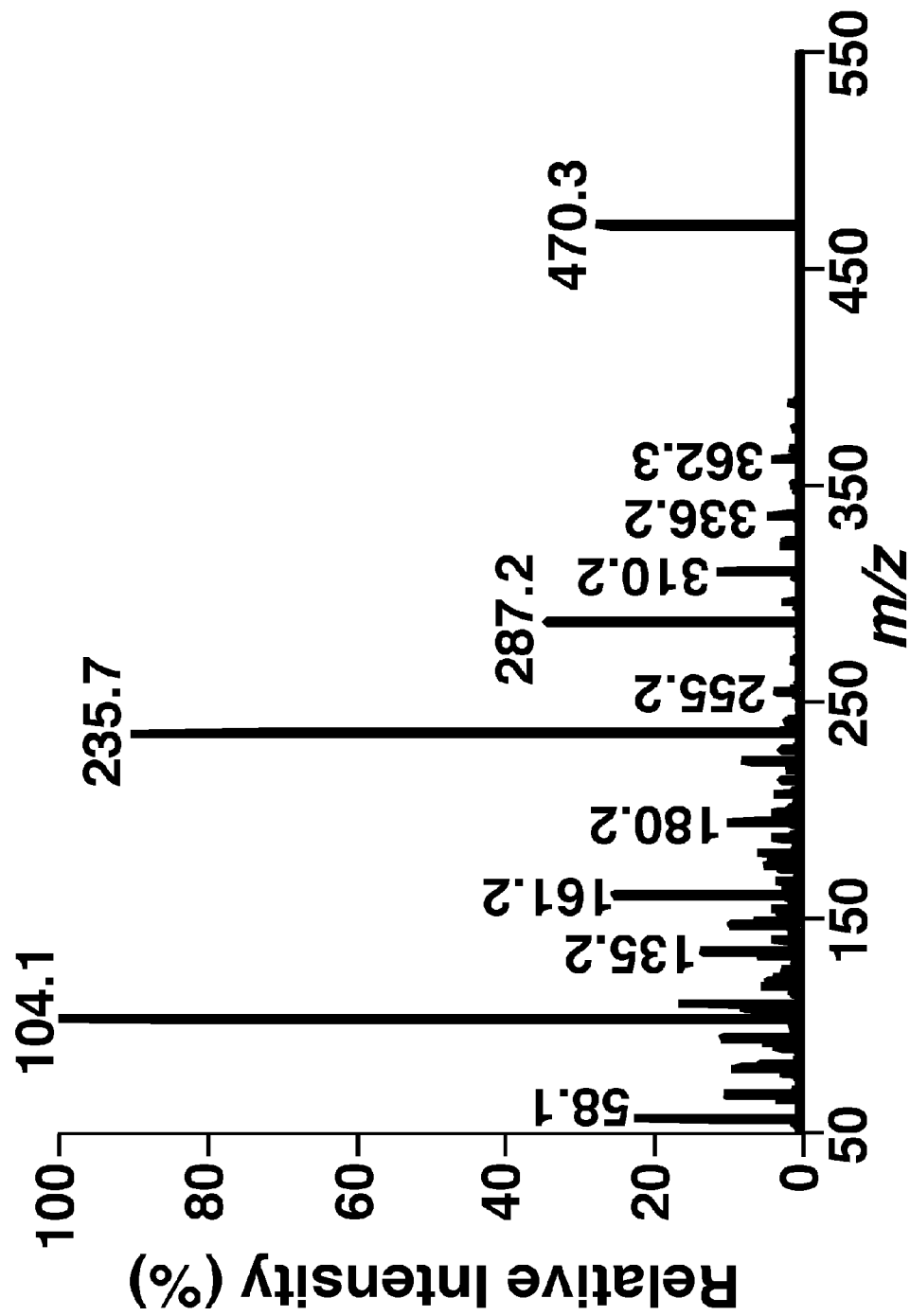
FIG. 11D represents doubly-charged 27-OH-Chol.

Large amounts of plasmalogen species were measured in the plasma lipids (FIG. 1A). Individuals having the earliest clinically recognizable stage of AD, exhibited a significant loss of plasmalogen molecular species without significant changes in the mass levels of diacyl GPEtn molecular species (FIG. 10B).

Example 8

Figure 12B:
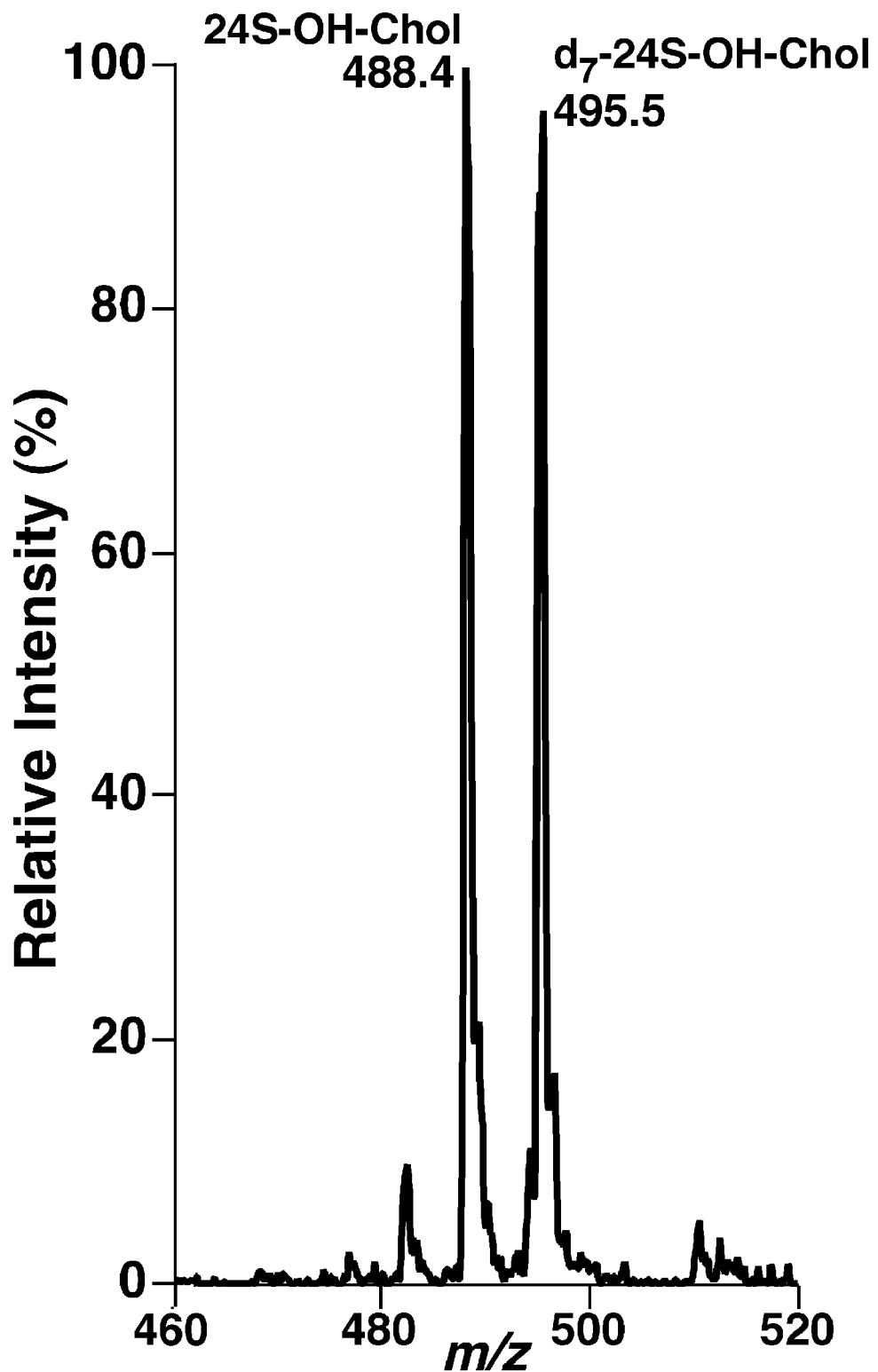
FIG. 12B shows the precursor ion analysis of an equimolar mixture of $d_7$-24S-OH-Chol and $d_7$-24S-OH-Chol.
Figure 12C:
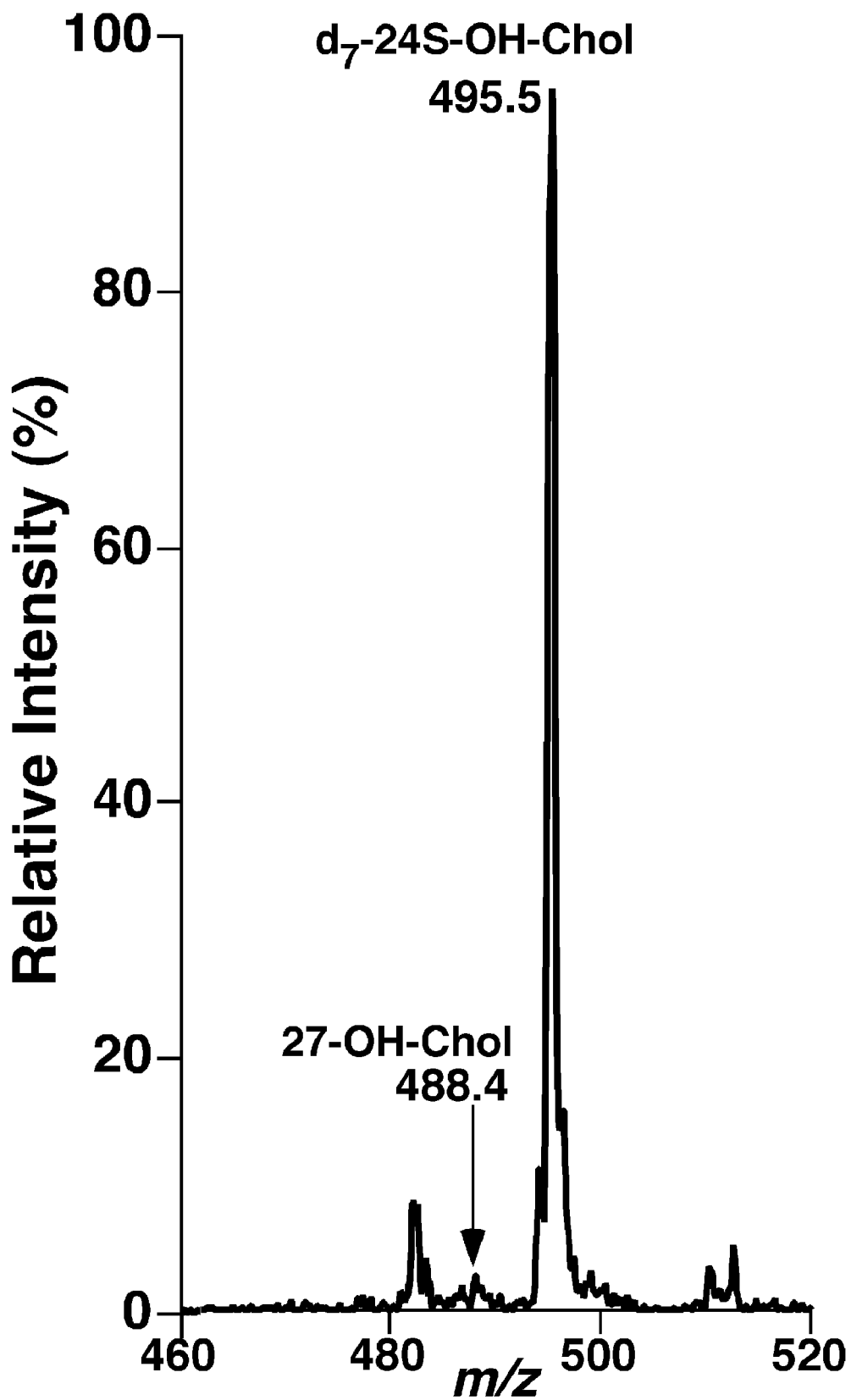
FIG. 12C shows the precursor ion analysis of an equimolar mixture of $2_7$—OH-Chol and $d_7$-24S-OH-Chol.

The Content of 24S-Hydroxycholesterol in Plasma and CSF Samples from Subjects with Very Mild Ad was Significantly Higher than that in Controls Elevated cholesterol mass levels may be a risk factor for AD due to its promotion of the production of amyloid-β peptides as described in Puglielli, L. et al. (2003) Alzheimer's disease: the cholesterol connection, Nat. Neurosci. 6, 345-351 and incorporated herein by reference. The increased mass level of cholesterol may lead to the accumulation of cytotoxic derivatives of oxidized cholesterol (e.g., 24S-OH-Chol), which is associated with AD. A mild and efficient method was developed for derivatization of primary, secondary, and tertiary alcohols using N,N-dimethylglycine (DMG), 1-ethyl-3-(3-dimethylamino-propyl)-carbodiimide, and 4-(N,N-dimethyl-amino) pyridine. By controlling the ratio of the derivatization reagents to the amount of alcohol, the reaction temperature, and/or the reaction time, one or both hydroxyl groups in oxysterols could be selectively derivatized. Characterization of these mono- or di-DMG derivatized oxysterols (including 24S-OH-Chol, 25-OH-Chol, 27-OH-Chol, and 7β-OH-Chol as well as 7-oxocholesterol, 5α,6α-epoxycholesterol, and 5β,6β-epoxycholesterol) show very different fragmentation patterns, which have the potential to be used to quantify their parent oxysterols in biological samples using the shotgun lipidomics approach. Examples of the distinct fragment patterns after CID of both mono-DMG and di-DMG derivatized 24S-OH-Chol and 27-OH-Chol are shown in FIG. 12.

Specific fragment(s) from each oxysterol can be selected from its mono-DMG or di-DMG derivative (or both) for quantitation by comparison to a deuterated internal standard. To confirm that there are no interfering contributions from other oxysterol isomers, the effects of other potential oxysterols on the quantitation must be examined. Individually mixed solutions of 24S-, 25-, 5α-, 5β-, 7α-, 7β-, or 27-OH-Chol with side chain deuterium labeled 24S-OH-Chol (i.e., $d_7$-24S-OH-Chol) in equal molar amounts were examined by precursor-ion scanning of m/z 283.4 (FIG. 12A). These results indicated that the influence of the other oxysterol isomers on the quantitation of 24S-OH-Chol by shotgun lipidomics is minimal and can be ignored even at equimolar levels with 24S-OH-Chol with experimental error (<5%).

This approach was used to quantify the mass levels of 24S-OH-Chol in plasma and CSF samples from individuals with very mild AD and from controls. The mass levels of 24S-OH-Chol in plasma from AD patients were significantly higher than that in controls (i.e., 46.2±5.3 ng/ml (n=4) in control vs. 60.8±6.1 ng/ml in AD (n=4), p<0.05).

Example 9

Plasma Lipid Profiles Differentiated Subjects with Very Mild AD from Cognitively Normal Controls The levels of approximately 100 lipid molecular species (Table 26 and 27) in lipid extracts of plasma from 6 individuals at the very mild stage of AD and from 6 controls, both verified by autopsies, were quantitated using shotgun lipidomic techniques. The lipid classes measured included: GPCho, lysoGPCho, ceramide, SM, S1P, DHS1P, and free fatty acids. Statistical analyses of the determined lipid molecular species from these samples were conducted using SAS (v9.1.3; SAS Institute, Cary, N.C.). Interactions among 106 lipid molecular species in these classes were analyzed using PROC GLM. Comparisons among the means of the disease group with the control group were performed using Duncan's multiple tests of two-sample t-tests where appropriate. Differences in the means between the disease and normal groups were designated as being significant if p<0.05 (or otherwise as indicated). The Pearson correlation test was performed on lipid mass levels across individual molecular species using SAS Proc CORR and Proc REG. Stepwise multi-variate regression implemented in SAS (using Proc REG) was used to identify independent predictors of AD. It was found that 18.1-22.6 dGPCho (p<0.0044), S1P (p<0.0179), DHS1P (p<0.0376), and the sum of S1P and DHS1P (p<0.0121) in subjects at the earliest stage of AD were significantly lower than those in cognitively normal controls. The sum of S1P and DHS1P was positively correlated with S1P and DHS1P. The analytical results showed that the subjects at the earliest stage of AD can be identified by the mass levels of 18:1-22:6 dGPCho and the sum of S1P and DHS1P mass levels as obtained by stepwise multivariate regressions analysis ($R^2$=0.8157, p<0.0073):

$$Z = 2.69213 - 0.17282X - 1.09366Y$$

where Z is a prediction factor of approximately 0 (varied from −0.091 to 0.283) for controls or 1 (varied from 0.695 to 1.090) for very mild AD, X is the mass level of 18:1-22.6 dGPCho and Y is the sum of S1P and DHS1P mass levels in nmol/mg protein. These results demonstrated that the determined lipid profile of 106 molecular species possessed a high selectivity to differentiate AD subjects at the very mild stage from controls.

TABLE 26

Analyzed free fatty acid, ceramide, lysoPC, PC, and sphingomyelin molecular species.

| Free Fatty Acid | Ceramide | LysoGPCho | GPCho | Sphingomyelin |
|---|---|---|---|---|
| F14:1 | N16:0 | 14:1 LPC | D16:1-16:1 | N15:2 |
| F14:0 | N18:0 | 14:0 LPC | D16:1-16:0 | N15:0 |
| F15:1 | N20:0 | 15:1 LPC | D16:0-18:2 | N16:1 |
| F15:0 | N22:0 | 15:0 LPC | D16:0-18:1 | N16:0 |
| F16:1 | N23:0 | 16:1 LPC | A16:0-20:4 | N17:1 |
| F16:0 | N24:2 | 16:0 LPC | D16:0-20:4/ D18:2-18:2 | N17:0 |
| F17:0 | N24:1 | 17:1 LPC | D18:1-18:2 | N18:1 |
| F18:3 | N24:0 | 18:2 LPC | D18:0-18:2/ D18:1-18:1 | N18:0 |
| F18:2 | hyro_N24:1 | 18:1 LPC | P18:0-20:4 | N24:2 |
| F18:1 |  | 18:0 LPC | D16:0-22:6 | N24:1 |
| F18:0 |  | 20:4 LPC | D18:1-20:4 | N24:0 |

TABLE 26-continued

Analyzed free fatty acid, ceramide, lysoPC, PC, and sphingomyelin molecular species.

| Free Fatty Acid | Ceramide | LysoGPCho | GPCho | Sphingomyelin |
|---|---|---|---|---|
| F19:0 | | 20:3 LPC | D18:0-20:4 | |
| F20:4 | | 22:6 LPC | D18:1-22:6 | |
| F20:3 | | | D18:0-22:6 | |
| F22:6 | | | | |

TABLE 27

Analyzed GPEtn and lysoGPEtn molecular species.

| GPEtn | GPEtn (Continued) | LysoGPEtn | |
|---|---|---|---|
| D16:1-16:1 | P18:0-20:4/P18:1-20:3/P16:0-22:4 | P16:1 | S1P |
| D14:1-16:1 | P18:1-20:2/P18:0-20:3/P16:0-22:3 | P16:0/15:1 | DHS1P |
| P16:0-16:1/P18:0-14:1 | P20:1-18:1/P18:1-20:1 | 15:0 | |
| D14:0-18:1/D16:0-16:1 | P18:1-20:0/D18:1-19:1 | 16:2 | |
| P16:0-18:2/P18:1-16:1 | D16:2-22:6/P20:0-18:0/P18:0-20:0 | 16:1 | |
| P18:1-16:0/P16:0-18:1 | D16:1-22:6 | 16:0 | |
| P18:0-16:0/P16:0-18:0 | D16:0-22:6 | P18:2 | |
| D16:1-18:2 | D16:0-22:5/D18:1-20:4 | P18:1/17:2 | |
| D16:0-18:2/D16:1-18:1 | D18:0-20:4/D16:0-22:4 | P18:0/17:1 | |
| D16:0-18:1 | D18:1-20:2/D16:0-22:3/D18:0-20:3 | 18:2 | |
| P14:0-22:6 | P18:2-22:6/D18:1-20:1 | 18:1 | |
| P16:1-20:4/P14:0-22:5 | P18:1-22:6/D18:0-20:1 | 18:0 | |
| P16:0-20:4/P14:0-22:4 | P18:0-22:6/P18:1-22:5/D18:0-20:0 | 19:2 | |
| P18:1-18:2/P16:0-20:3 | P18:0-22:5/P18:1-22:4 | 19:1 | |
| P18:1-18:1/P18:0-18:2/P16:0-20:2 | P18:0-22:4/P20:0-20:4/P18:1-22:3 | 19:0 | |
| P18:0-18:1/P16:0-20:1 | A20:0-20:4/P18:0-22:3 | 20:4 | |
| A18:0-18:1 | A18:0-22:3/P18:0-22:2 | 20:3 | |
| D14:1-22:6 | D18:2-22:6 | 20:2 | |
| D16:2-20:4/D14:1-22:5 | D18:1-22:6 | 22:6 | |
| D16:1-20:4 | D18:0-22:6/D18:1-22:5 | 22:5 | |
| D16:0-20:4/D18:2-18:2 | D18:1-22:4/D18:0-22:5 | 22:4 | |
| D18:1-18:2/D16:0-20:3 | D20:0-20:4/D18:1-22:3/D18:0-22:4 | | |
| D18:0-18:2/D18:1-18:1/D16:0-20:2 | D20:0-20:3/D18:0-22:3 | | |
| D18:0-18:1/D16:0-20:1 | D20:0-20:2/D18:0-22:2 | | |
| P16:0-22:6/D18:0-18:0/P18:2-20:4 | D20:0-20:1/D18:0-22:1 | | |
| P18:1-20:4/P16:0-22:5 | D20:0-20:0/D18:0-22:0 | | |

Example 10

Altered Plasma Lipid Profiles

There are at least three specialized lipid alterations present in brain samples of AD subjects with mild cognitive impairment (MCI). In preliminary studies (see Examples 4, 8, and 9 above), multiple lipid classes and/or molecular species have been identified (e.g., S1P, DHS1P, 24S-OH-Chol, and plasmalogen) as altered in the plasma sample from individuals at the earliest clinically recognizable stage of AD (i.e., MCI). Although a single alteration in individual lipid molecular species may not be sufficiently sensitive to independently serve as an effective biomarker for the early diagnosis of AD, the entire plasma lipid profile which includes all lipid molecular species that can be identified and quantified using shotgun lipidomics collectively may serve as a much more effective and accurate biomarker with very high sensitivity and specificity.

The lipid profiles of plasma samples (~0.5 ml) may be tested to determine if the lipid profile can differentiate subjects who have a clinical dementia rating (CDR) score of 0 (control) from subjects with a CDR score of 0.5 (i.e., MC1) or greater due to AD with high sensitivity and specificity. Over 20 lipid classes and 1000 lipid molecular species from lipid extracts of each plasma sample may be assessed using shotgun lipidomics and analyzed using stepwise multivariate regression analysis.

Based on previous data (see Example 4, 8, and 9 above), power analysis revealed that 30 subjects are required per group to have a 95% confidence interval of sensitivity of between 1.2% and 3.6% across the range of specificity between 60% and 90%. Although even fewer numbers of subjects may be required to achieve such sensitivity and specificity with increasing numbers of lipid alterations in the plasma lipidome of AD patients with CDR 0.5, 30 subjects per group may be tested.

Inclusion and exclusion criteria for subjects may be by age (60-85 years), and having no history of chronic medical disease, head trauma, stroke, or other neurological disease (unless specified). Fasting plasma samples from preliminary studies have been retrospectively collected by the clinical core of the Alzheimer's Disease Research Center (ADRC) at Washington University School of Medicine from volunteer subjects longitudinally followed at the Washington University Memory and Aging Project (ages 60-85) for over 15 years. These samples have been stored in the sample core of the Center and may be obtained for the studies contingent upon approval from the core committee. In addition, 30 or more subjects per group that are CDR 0.5, 1, and 2 may be assessed. The sample core of ADRC has already procured most of the samples, and additional samples may be obtained in collaboration with Dr. Burns in the Department of Neurology, University of Kansas Medical Center.

Example 11

The Entire Plasma Lipid Profile May Differentiate Subjects with AD-Type Cognitive Dementia from Those with Other Neurodegenerative or CNS Diseases with High Sensitivity and Specificity An effective biomarker for the early diagnosis of AD should differentiate subjects with AD-type cognitive dementia at the very early stages from those with other neurodegenerative diseases with high sensitivity and specificity. Sulfatide loss in the brain and CSF samples from subjects at the earliest clinically recognizable stage of AD is very specific relative to PD and dementia with Lewy bodies, both of which are compounded in the clinical diagnosis. Although it is unknown if each individual lipid change in the plasma lipidome present in AD patients will be specific to AD, it is highly likely that the entire lipid profile of the plasma lipidome will be able to differentiate patients with AD-type dementia from those with other neurodegenerative diseases. In this study, the specificity of the entire plasma lipid profile as a biomarker for AD may be determined.

Shotgun lipidomics may be used to examine plasma lipid profiles from subjects with front-temporal dementia, PD, and multiple sclerosis. Over 20 lipid classes and approximately 1000 lipid molecular species from lipid extracts of each sample may be examined. The determined mass levels of each individual lipid molecular species may be analyzed by stepwise multivariate regression analysis.

At least 30 plasma samples per disease group may be used. Inclusion and exclusion criteria for subjects may be by age (60-85 years), and having no history of chronic medical disease, head trauma, stroke, or other neurological disease (unless specified). Fasting plasma samples from preliminary studies have been retrospectively collected by the clinical core of the Alzheimer's Disease Research Center (ADRC) at Washington University School of Medicine from volunteer subjects longitudinally followed at the Washington University Memory and aging Project (ages 60-85) for over 15 years. These samples have been stored in the sample core of the Center and may be obtained for the studies contingent upon approval from the core committee. In addition, 30 or more subjects per group that are CDR 0.5, 1, and 2 may be assessed. The sample core of ADRC has already procured most of the samples, and additional samples may be obtained in collaboration with Dr. Burns in the Department of Neurology, University of Kansas Medical Center.

Once diagnostic plasma lipid profiles from the above studies are identified, the biomarker profiles may be validated further by two independent means to identify their specificity. First, the plasma samples may be analyzed and categorized from the sample core of ADRD at Washington University School of Medicine in a blinded fashion. Second, blinded plasma samples from outside sample providers may be characterized and classified to identify the disease states.

Example 12

The Entire Plasma Lipid Profile May Differentiate Subjects with AD-Type Cognitive Dementia from Those with Normal Aging Multiple lines of evidence indicate that a pre-clinical state of AD occurs 5 to 10 years prior to the mild cognitive impairment (MC1) clinically diagnosed as the earliest stage of AD. Detection of this pre-clinical stage may make therapeutic treatment to delay or prevent the disease onset much more effective. Previous results from the determination of lipid alterations in post-mortem brain samples indicated that lipid profiles in the brain at the pre-clinical stage of AD were undergoing substantial changes (see Example 2). The plasma lipid profile may also be altered at this stage relative to normal aging (see Examples 4, 8, and 9 above). Shotgun lipidomics may be used to determine the entire plasma profile of individuals whose parents did or did not have AD prior to the age of 80.

Shotgun lipidomics analysis of plasma lipid profiles may be performed to determine whether an altered plasma lipid profile exists that is associated with the possible pre-clinical stage of AD. Plasma samples from an existing longitudinal study at the ADRD at Washington University School of Medicine may be used. Plasma samples (1 ml) may be shared from the existing study from the following ages (45-54, N=20; 55-64, N=20; and 65-74, N=20). The determined mass levels of each individual lipid molecular species may be analyzed by stepwise multivariate regression analysis.

Inclusion and exclusion criteria for subjects may be by age (45-74 years), and having no history of chronic medical disease, head trauma, stroke, or other neurological diseases. Fasting plasma samples from preliminary studies have been collected by the clinical core of the Alzheimer's disease Research Center (ADRC) at Washington University School of Medicine from volunteer subjects longitudinally followed at the Washington University Healthy Aging and Senile Dementia Project. These samples have been stored in the sample core of the Center and may be obtained for the studies contingent upon approval from the core committee. In addition, 30 or more subjects per group that are CDR 0.5, 1, and 2 may be assessed. The sample core of ADRC has already procured most of the samples, and additional samples may be obtained in collaboration with Dr. Burns in the Department of Neurology, University of Kansas Medical Center.

Example 13

The Level of Sulfatides May Differentiate Subjects with AD-Type Cognitive Dementia from Those with Normal Aging A highly beneficial biomarker for the early diagnosis of AD should not only differentiate subjects with AD-type cognitive dementia at the very early stages from those with other neurodegenerative diseases with high sensitivity and specificity, it should also be detectable through a minimally invasive procedure. Sulfatide loss in the brain and CSF samples from subjects at the earliest clinically recognizable stage of AD is very specific relative to PD and dementia with Lewy bodies, suggesting sulfatides are likely candidates for effective biomarkers for the early diagnosis of AD. While the sulfatide loss may be detected in brain tissue and CSF samples, it would be more beneficial if the sulfatide loss could be detected through a less invasive means such as in plasma samples.

To determine if the AD-associated sulfatide loss could be detected through a less invasive means, lipid extracts of human plasma samples (500 µl each) were prepared by using a modified Bligh and Dyer procedure, as described in Example 1, in the presence of 0.5 nmol/ml of plasma. The plasma samples were obtained from two non-AD patients and two AD patients at the earliest clinically recognizable stage of AD. The lipid extracts were reconstituted in 500 µl of chloroform/methanol (1:1, by volume). Part of the solution (100 µl) was treated with lithium methoxide and the sphingolipids in the alkaline-treated lipid solutions were recovered as described in Example 1. The recovered sphingolipids were dissolved in 100 µl of chloroform/methanol (1:1, by volume) and 20 µl was diluted to 200 µl with isopropanol/acetonitrile (60/40, v/v). After mixing 10 µl of diluted sample with 10 µl of 9-aminoacridine (10 mg/ml; dissolved in isopropanol/acetonitrile (60/40, v/v)), 0.25 µl of the mixture was spotted on an Opti-TOF® 384 well plate in a low humidity environment as described in the art (Sun, G., Yang, K., Zhao, Z., Guan, S., Han, X., and Gross, R. W. (2007) Shotgun metabolomics approach for the analysis of negatively charged water-soluble cellular metabolites from mouse heart tissue, Anal. Chem. 79, 6629-6640). Mass Spectrometric analysis of sulfatides was performed on a 4800 MALDI TOF/TOF Analyzer in the negative ion mode by averaging 1500 consecutive laser shots (50 shots per subspectra and 30 subspectra) with default calibration. Tandem mass spectrometric analyses of lipids were accomplished by collision-induced dissociation (CID) gas using air at medium pressure.

From preliminary studies of two control and two AD patients, the levels of sulfatides in plasma samples were found to be 0.55 and 0.58 nmol/ml of plasma in cognitively normal controls and 0.41 and 0.36 nmol/ml of plasma in AD patients. The results indicated that the level of sulfatides in the plasma of AD individuals was approximately 20% lower than those of controls. The AD-associated sulfatide loss could be detected in human plasma sample, therefore providing a less invasive means by which a highly effective biomarker for the early diagnosis of AD could be detected.

What is claimed is:

1. A biomarker for detecting a neurological disorder, wherein the biomarker is a regression value derived from a lipid profile obtained by shotgun lipidomics, wherein the regression value is a single value, derived from stepwise multivariate regression analysis, that is sensitive to changes in abundance of lipid molecular species of the lipid profile, wherein a regression value of about 1 is indicative of a neurological disorder.

2. The biomarker of claim 1, wherein the lipid profile comprises lipids from at least 15 different lipid classes.

3. The biomarker of claim 2, wherein the lipid profile comprises lipids from at least 20 different lipid classes.

4. The biomarker of claim 3, wherein the lipid classes are selected from the group consisting of choline glycerophospholipid, ethanolamine glycerophospholipid, phosphatidylinositol, phosphatidylglycerol, phosphatidylserine, lyso-choline glycerophospholipid, lyso-ethanolamine glycerophospholipid, phosphatidic acid, lyso-phosphatidic acid, sphingomyelin, galactosylceramide, glucosylceramide, sulfatide, free fatty acid, prostaglandins, triacylglycerol, diacylglycerol, monoacylglycerol, acyl-CoA, acylcarnitine, cholesterol and cholesterol esters, oxysterol, ceramide, cardiolipin, sphingoid base-1-phosphate, shingosine, lyso-sphingomyelin, gangliosides, and oxidized derivatives of each of the above.

5. The biomarker of claim 3, wherein the lipid classes are selected from the group consisting of plasmalogen, sulfatide, ceramide, sphingoid base-1-phosphates, cholesterol, and cholesterol esters.

6. The biomarker of claim 1, wherein the lipid profile further comprises lipids from at least 75 different lipid molecular species.

7. The biomarker of claim 6, wherein the lipid profile further comprises lipids from at least 100 different lipid molecular species.

8. The biomarker of claim 7, wherein the lipid molecular species are selected from the group consisting of over 1000 lipid molecular species.

9. The biomarker of claim 1, wherein the neurological disorder is selected from the group consisting of Alzheimer's disease (AD), pre-AD, Parkinson's disease, multiple sclerosis, fronto-temporal dementia, bipolar disorder, or schizophrenia.

10. The biomarker of claim 1, wherein the lipid profile is a plasma lipid profile or a lipid profile of cerebrospinal fluid.

* * * * *